US008466274B2

(12) United States Patent
Tang

(10) Patent No.: US 8,466,274 B2
(45) Date of Patent: *Jun. 18, 2013

(54) RNAI THERAPEUTIC FOR TREATMENT OF HEPATITIS C INFECTION

(71) Applicant: Hengli Tang, Tallahassee, FL (US)

(72) Inventor: Hengli Tang, Tallahassee, FL (US)

(73) Assignee: Florida State University Research Foundation, Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/633,199

(22) Filed: Oct. 2, 2012

(65) Prior Publication Data

US 2013/0028964 A1 Jan. 31, 2013

Related U.S. Application Data

(62) Division of application No. 13/034,851, filed on Feb. 25, 2011, now Pat. No. 8,318,925, which is a division of application No. 12/167,402, filed on Jul. 3, 2008, now Pat. No. 7,910,722.

(60) Provisional application No. 60/948,040, filed on Jul. 5, 2007.

(51) Int. Cl.
*C07H 21/04* (2006.01)
*C07H 21/02* (2006.01)
*A61K 48/00* (2006.01)
*C12N 15/63* (2006.01)

(52) U.S. Cl.
USPC ... 536/24.5; 536/23.1; 536/24.31; 536/24.33; 514/44; 435/320.1

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 4,920,016 | A | 4/1990 | Allen et al. |
| 5,019,369 | A | 5/1991 | Presant et al. |
| 2008/0113351 | A1 | 5/2008 | Naito et al. |
| 2008/0113369 | A1 | 5/2008 | Khvorova et al. |
| 2008/0113370 | A1 | 5/2008 | Khvorova et al. |
| 2008/0113371 | A1 | 5/2008 | Khvorova et al. |
| 2008/0113930 | A1 | 5/2008 | Tan et al. |
| 2008/0113931 | A1 | 5/2008 | Constien |
| 2008/0114281 | A1 | 5/2008 | Birchall et al. |

FOREIGN PATENT DOCUMENTS

WO    WO 2004/038003    5/2004

OTHER PUBLICATIONS

Barik, S., "Immunophilins: for the love of proteins", Cell. Mol. Life Sci. 63:2889-2900, (2006).

Bergsma, D.J., et al., The cyclophilin multigene family of peptidyl-prolyl isomerases. Characterization of three separate human isoforms. J. Biol. Chem. 266; 23204-23214, (1991).
Binder, M., et al., "Identification of determinants involved in initiation of hepatitis C virus RNA synthesis by using intergenotypic replicase chimeras", J. Virol. 81:5270-5283, (2007).
Braaten, D., et al., "The hydrophobic pocket of cyclophilin is the binding site for the human immunodeficiency virus type 1 Gag polyprotein", J. Virol, 71:2107-2113, (1997).
Braaten, D., et al., "Cyclophilin A regulates HIV-1 infectivity, as demonstrated by gene targeting in human T cells", EMBO J. 20:1300-1309, (2001).
Cai, Z., et al., "Robust production of infectious hepatitis C virus (HCV) from stably HCV cDNA-transfected human hepatoma cells", J. Virol. 70:13963-13973, (2005).
Evans, M.J., et al., "Phosphorylation of hepatitis C virus nonstructural protein 5A modulates its protein interactions and viral RNA replication", Proc. Natl. Acad. Sci. USA 101:13038-13043, (2004).
Fernandes, F., et al., Sensitivity of hepatitis C virus to cyclosporine A depends on nonstructural proteins NS5A and NS5B. Hepatology 46: 1026-1033, (2007).
Gamble, T.R., et al., "Crystal structure of human cyclophilin A bound to the amino-terminal domain of HIV-1 capsid", Cell 87:1285-1294, (1996).
Gosert, R., et al., Identification of the hepatitis C virus RNA replication complex in Huh-7 cells harboring subgenomic replicons, J. Virol. 77:5487-5492, (2003).
Hamamoto, I., et al. "Human VAP-B is involved in hepatitis C virus replication through interation with NS5A and NS5B", J. Virol, 79:13473-13482, (2005).
Handschumacher, R.E., et al., "Cyclophilin: a specific cytosolic binding protein for cyclosporine A," Science, 226:544-547, (1984).
Inoue, K., et al., "Evaluation of a cyclophilin inhibitor in hepatitis C virus-infected chimeric mice in vivo", Hepatology 45:921-928, (2007).

(Continued)

*Primary Examiner* — Amy Bowman
(74) *Attorney, Agent, or Firm* — Alchemy-Partners, PC

(57) ABSTRACT

Small interfering RNAs (siRNAs) or small hairpin RNA (shRNAs) and compositions comprising same are provided that target human cyclophilin A (CyPA) to inhibit Hepatitis C (HCV) infection. Such siRNA and shRNAs may have a length of from about 19 to about 29 contiguous nucleotides corresponding to a specific region of human cyclophilin A (CyPA) cDNA of from about nucleotide 155 to about nucleotide 183 having particular potency against CyPA and HCV. Such siRNA and shRNAs may be formulated as naked compositions or pharmaceutical compositions. DNA polynucleotides, plasmids, and viral or non-viral vectors are also provided that encode siRNA or shRNA molecules, which may be delivered directly to cells or in combination with delivery agents, such as lipids, polymers, encapsulated lipid particles, such as liposomes. Methods for treating, managing inhibiting, preventing, etc., HCV infection using such siRNA and shRNAs and compositions comprising same are also provided.

21 Claims, 7 Drawing Sheets

OTHER PUBLICATIONS

Ishii, N., et al., "Diverse effects of cyclosporine on hepatitis C virus strain replication", J. Virol. 80:4510-4520, (2006).
Ke., H., et al., "Crystal structure of murine cyclophilin C complexed with immunosuppressive drug cyclosporine A", Proc. Natl. Acad. Sci., USA, 90:11850-11854, (1993).
Kozutsumi, Y., The presence of malfolded proteins in the endoplasmic reticulum signals the induction of glucose-regulated proteins. Nature 332:462-464, (1988).
Lindenbach, B.D., et al., "Complete replication of hepatitis C virus in cell culture", Science 309:623-626, (2005).
Lindenbach, B.D., et al. "Unravelling hepatitis C virus replication from genome to function", Nature 436:933-938, (2005).
Liu, J., et al., "Calcineurin is a common target of cyclophilin-cyclosporin A and FKBP-FK506 complexes", Cell 66:807-815, (1991).
Luban, J., "Cyclophilin A, TRIM5, and resistance to human immunodeficiency virus type 1 infection", J. Virol. 81:1054-1061. (2007).
Luban, J., et al., "Human immunodeficiency virus type 1 Gag protein binds to cyclophilins A and B," Cell 73:1067-1078, (1993).
Ma, S., et al. "NIM811, a cyclophilin inhibitor, exhibits potent in vitro activity against hepatitis C virus alone or in combination with alpha interfero," Antimicrob. Agents Chemother. 50:2976-2982, (2006).
Mikol, V., et al., X-ray structure of a cyclophilin B/cyclosporine complex: comparison with cyclophilin A and delineation of its calcineurin-binding doman, Proc. Natl. Acad Sci. USA 91:5183-5186, (1994).
Miyanari, Y., et al. "Hepatitis C virus non-structural proteins in the probable membranous compartment function in viral genome replication. J. Biol. Chem," 278:50301-50308, (2003).
Moradpour, D., et al. "Insertion of green florescent protein into nonstructural protein 5A allows direct visualization of functional hepatitis C virus replication complexes," J. Virol. 78:7400-7409, (2004).
Munro, S., et al., "An Hsp70-like protein in the ER: identity with the 78 kd glucose-regulated protein and immunoglobulin heavy chain binding protein," Cell 46:291-300, (1986).
Nakagawa, M., et al. "Specific inhibition of hepatitis C virus replication by cyclosporine A," Biochem. Biophys. Res. Commun. 313:42-47, (2004).
Nakagawa, M., et al., "Suppression of hepatitis C virus replication by cyclosporine a is mediated by blockade of cyclophilins", Gastroenterology 129:1031-1041, (2005).
Nelson, H.B., et al., "The effect of cell growth of hepatitis C virus (HCV) replication and a mechanism of cell confluence-based inhibition of HCV RNA and protein expression", J. Virol. 80:1181-1190, (2006).
Neri, P., et al., "NMR studies of [U-13C] cyclosporine A bound to human cyclophilin B," FEBS Lett. 290:195-199, (1991).
Okamoto, T., et al., "Hepatitis C virus RNA replication is regulated by FKBPS and Hsp90," EMBO J. 25:5015-5025, (2006).
Paeshuyse, J., et al., "The non-immunosupressive cyclosporine DEBIO-025 is a potent inhibitor of hepatitis C virus replication in vitro", Hepatology 43:761-770, (2006).
Paslaru, L., et al., "GRP78 induction by cyclosporin A in human HeLa cells, FEBS Lett. 350:304-308, (1994).
Pfugli, G., et al., "X-ray structure of a decameric cyclophilin-cyclosporin crystal complex", Nature 361:91-94, (1993).
Quinkert, D., et al., "Quantitative analysis of the hepatitis C virus replication complex", J. Virol. 79:13594-13605, (2005).
Robida, J.M., et al., "Characterization of hepatitis C virus subgenomic replicon resistance to cyclosporine in vitro", J. Virol. 81:5829-5840, (2007).
Salonen, A., et al., "Viral RNA replication in association with cellular membranes", Curr. Top. Microbiol. Immunol. 285:139-173, (2005).
Sayah, D.M., "Cyclophilin A retrotransposition into TRIM5 explains owl monkey resistance to HIV-1", Nature 430:569-573, (2004).
Sokolskaja, E., et al., "Cyclophilin, TRIM5, and innate immunity to HIV-1", Curr. Opin. Microbol. 9:404-408, (2006).

Stone, M., et al., "Participation of rab5, an early endosome protein, in hepatitis C virus RNA replication machinery", J. Virol. 81:4551-4563, (2007).
Vajods, F.F., et al., "Crystal structure of cyclophilin A complexed with a binding site peptide from the HIV-1 capsid", Protein Sci. 6:2297-2307, (1997).
Wakita, T., et al., "Production of infectious hepatitis C virus in tissue culture from a cloned viral genome", Nat. Med. pp. 1-6, (2005).
Wang, C., et al., "Identification of FBL2 as a geranylgeranylated cellular protein required for hepatitis C virus RNA replication", Mol. Cell 18:425-434, (2005).
Waninger, S., et al., "Identification of cellular cofactors for human immunodeficiency virus replication via a ribozyme-based genomics approach", J. Virol. 78:12829-12837 (2004).
Watashi, K., et al., "Cyclosporin A suppresses replication of hepatitis C virus genome in cultured hepatocytes", Hepatology 38:1282-1288, (2003).
Watashi, K., et al., "Cyclophilin B is a functional regulator of hepatitis C virus RNA polymerase", Mol. Cell 19:111-122, (2005).
Yi, M., et al., "Production of infectious genotype 1a hepatitis C virus (Hutchinson strain) in culture human hepatoma cells", Proc. Natl. Acad. Sci. USA 103:2310-2315, (2006).
Zhao, Y., et al., "Cyclophilin A complexed with a fragment of HIV-1 gag protein: insights into HIV-1 infectious activity", Structure 5:139-146 (1997).
Zhong, J., et al., "Robust hepatitis C virus infection in vitro", Proc. Natl. Acad. Sci. USA 102:9294-9299, (2005).
Fire, et al., Nature, 391, 806 (1998).
Fire et al., "RNA-trigered gene silencing", Trends Genet., 15(9): 358-63, (1999).
Bernstein, et al., "Role for a bidentate ribonuclease in the initiation step of RNA interference", Nature, 409:363 (2001).
Elbashir, S.M., et al., "RNA interference is mediated by 21- and 22-nucleotide RNAs", Genes Dev. 15:188, (2001).
Inoue, K., et al., "Combined interferon a2b and cyclosporine A in the treatment of chronic hepatitis C: controlled trial", Journal of Gastroenterology 38(6):567-72, (2003).
De Paula, E., et al., "Hydrophobization and bioconjunction for enhanced siRNA delivery and targeting", RNA 13:431-56, (2007).
Chen, Y., et al., "RNAi for treating hepatitis B viral infection", Pharmaceutical Research 25(1); 72-86, (2008).
Kim, D., et al., "RNAi mechanisms and applications", Biotechniques 44(5):613-16, (2008).
Tuschl, T., "Expanding small RNA interference", Nat. Biotechnol. 20(5):446-448, (2002).
Brummelkamp, T.R., et al., "A system for stable expression of short interfering RNAs in mammalian cells", Science 296(5567); 550-553, (2002).
Miyagishi, M., et al., U6 promoter-driven siRNAs with four uridine 3' overhangs efficiently suppress targeted gene expression in mammalian cells. Nat. Biotechnol. (20(5):497-500, (2002).
Paddison, P.J., et al., "Short hairpin RNAs (shRNAs) induce sequence-specific silencing in mammalian cells", Genes Dev. 16(8):948-58, (2002).
Lee, N.S., et al. "Expression of small interfering RNSs targeted against HIV-1 rev transcripts in human cells", Nat. Biotechnol, 20(5):500-505, (2002).
Paul, C.P., et al., "Effective expression of small interfering RNA in human cells", Nat. Biotechnol. 20(5):505-508, (2002).
Dornburg, R., "Reticuloendotheliosis viruses and derived vectors", Gene Therap. 2:301-310, (1995).
Eglitis, M.A., "Retroviral vectors for introduction of genes into mammalian cells", Biotechniques 6(7):608-614, (1988).
Miller, A.D., Hum Gene Therap., 1:5-14, (1990).
Anderson, W.F., "Human gene therapy", Nature 392 (6679 Suppl.): 25-30, (1998).
Wang, Z. et al., "Inhibition of Trypanosoma brucei Gene Expression by RNA Interference Using an Integratable Vector with Opposing T7 Promoters", J. Biol. Chem. 275:40174-40179, (2000).
Lohmann, et al., "Replication of Subgenomic Hepatitis C Virus in a Hepatoma Cell Line", Science, 285:110-113, (1999).
Blight, et al., "Efficient initiation of MCV RNA replication in cell culture", Science 290:1972-1974, (2000).

Wakita, T., et al. "Production of hepatitis C virus in tissue culture from a cloned viral genome", Nature Medicine, 11(7):791-6, (2005).
Kapadia, S.B., et al., "Hepatitis C virus RNA replication is regulated by host geranylgeranylation and fatty acids", PNAS 102:2561-2566, (2005).
Kolykhalov, et al., "Transmission of hepatitis C by intrahepatic inoculation with transcribed RNA", Science 277:570-574, (1997).
Heckel, et al., "Neonatal bleeding in transgenic mice expressing urokinase-type plasminogen activator", Cell 62:447-456, (1990).
Szoka, et al., "Comparative properties and methods of preparation of lipid vesicles (liposomes)", Ann. Rev. Biophys. Bioeng. 9:467, (1980).
Sambrook, et al., Molecular Cloning: A Laboratory Manual, Second Edition, Cold Spring Harbor, N.Y., (1989).
Wolff, J.A., et al., "PNAS", 84:3344-3348, (1987).
Ledley, F.D., et al., "PNAS", 84:5335-5339, (1987).
Chowdhury, J.R., et al., "Science," 254: 1802, (1991).
Grossman, M. et al., "Nature", Genetics 6,335, (1994).
Kay, M.A., et al., "Hum Gene", Ther. 3: 641-647, (1992).
Ferry, N., et al., "PNAS", 88: 8377-8381, (1991).
Kaleko, M., et al., "Hum Gene", Ther. 2: 27-32 (1991).
Stratford-Perricaudet, L.D., et al., "Hum Gene", Ther. 1: 241, (1990).
Jaffe, H.A. et al., Nat. Genet. 1:372, (1992).
Li, Q. et al. Hum. Gene Ther. 4: 403 (1993).
Wu, G.Y., et al., J. Biol. Chem. 263: 14621-14624, (1988).
Malone, R.W., et al., JBC 269:29903-29907, (1994).
Hickman, M.A., Human Gene Therapy 5:1477-1483, (1994).
Kaneda, Y., et al., Biol. Chem. 264: 12126-12129, (1989).
Soriano, P., et al., PNAS 80:7128-7131, (1983).
Kaneda, Y., et al., Science 243:375-378, (1989).
Lee, et al., "Critical Reviews in Therapeutic Drug Carrier Systems", 8, 91-192, (1991).
Muranishi, "Critical Reviews in Therapeutic Drug Carrier Systems", 7, 1-33, (1990).
El-Hariri, et al., "The mitigating effects of phosphatidylcholines on bile salt- and lysophosphatidylcholine-induced membrane damage", J. Pharm. Pharmacol. 44, 651-654, (1992).
Buur, et al., J. Control Rel. 14, 43-51 (1990).
Takahashi, et al., J. Pharm. Pharmacol. 40, 252-257, (1988).
Yamashita, et al., J. Pharm. Pharmacol. 39, 621-626, (1987).
Sambrook J., et al., "Molecular Cloning: A Laboratory Manual", Cold Spring Harbor and its 3rd Ed. (2001).
Ausubel, F. M., Current Protocols in Molecular Biology, Greene Pub. Associates and Wiley-interscience, (1987).

Ausubel, F.M., "Short Protocols in Molecular Biology: A Compendium of Methods from Current Protocols in Molecular Biology", Greene Pub. Associates and Wiley ¬ interscience, (1989).
Innis, M.A., "PCR Protocols: A Guide to Methods and Applications", Academic Press, (1990).
Ausubel, F.M., "Short Protocols in Molecular Biology: A Compendium of Methods from Current Protocols in Molecular Biology", Wiley, & Sons, $5^{th}$ Ed., (2002).
Innis, M.A., et al., "PCR Strategies", Academic Press, (1995).
Ausubel, F.M., "Short Protocols in Molecular Biology: A Compendium of Methods from Current Protocols in Molecular Biology", Wiley, and annual updates, (1999).
Sninsky, J.J., et al., :PCR Applications: Protocols for Functional Genomics, Academic Press, (1999).
Sambrook J. et al., "Molecular Cloning: A Laboratory Manual", 3rd Ed., Cold Spring Harbor Laboratory Press, Cold Spring Harbor, N.Y., (2001).
Yang, F. et al. "Cyclophilin A is an essential cofactor for hepatitis C virus infection and the principal mediator of cyclosporine resistance in vitro", J. Virology 82(11):5269-78, (Jun. 2008).
Immordino, M.L., "Stealth liposomes: review of the basic science, rationale, and clinical applications, existing and potential", Int. J. Nanomedicine 1(3):297-315, (2006).
Samad, A., "Liposomal Drug Delivery Systems: An Update Review", Current Drug Delivery 4(4):297-305, (2007).
Pathak, A., "Nanovectors for efficient liver specific gene transfer", Int. J. Nanomedicine, 3(1):31-49, (2008).
Freshney, R.I., "Culture of Animal Cells: A Manual of Basic Technique", 4th Ed., (2000).
Spector, D.L., "Cells: A Laboratory Manual, Culture and Biochemical Analysis of Cells", Cold Spring Harbor Press, (1998).
Kneteman, N.M, et al., "Mice with Chimeric Human Livers: Who Says Supermodels Have to Be Tall?", Hepatology, pp. 703-706, (Apr. 2005).
Blight, K.J., et al., "Efficient Initiation of HCV RNA Replication in Cell Culture", Science, vol. 290, pp. 1972-1974, (Dec. 2000).
Straight, A.F., et al., "Mitosis in Living Budding Yeast: Anaphase a But No Metaphase Plate", Science, vol. 277, (Jul. 1997).
Scherer, et al., "Approaches for the Sequence-Specific Knockdown of mRNA", 2003, Nat. Biotechnol., 21(12), pp. 1457-1465.
Mahato, et al., "Modulation of Gene Expression by Antisense and Antigene Oligodeoxynucleotides and Small Interfering RNA", Jan. 2005, Expert Opinion on Drug Delivery, vol. 2, No. 1, pp. 3-28.
Zhang et al., "Targeted Gene Silencing by Small Interfering RNA-Based Knock-Down Technology", 2004, Current Pharmaceutical Biotechnology, vol. 5, pp. 1-7.

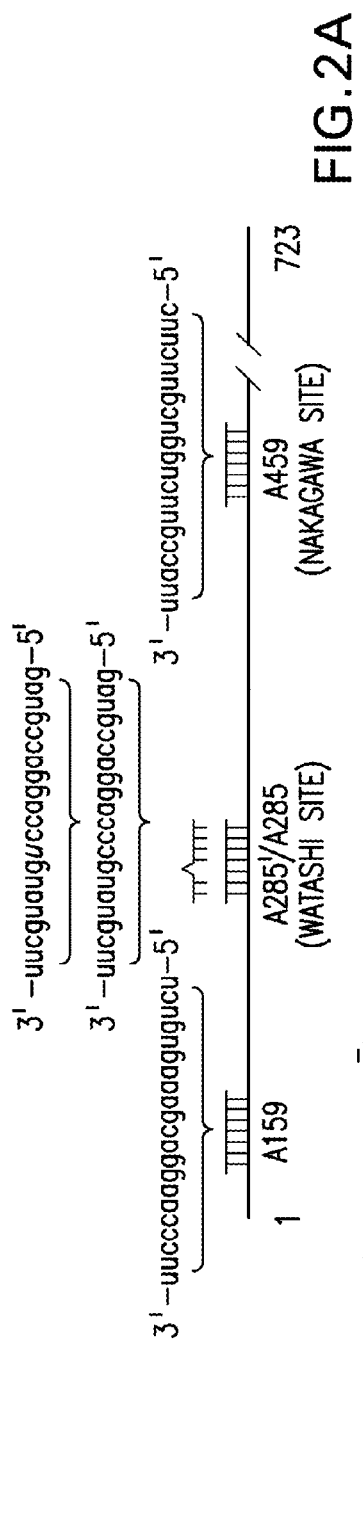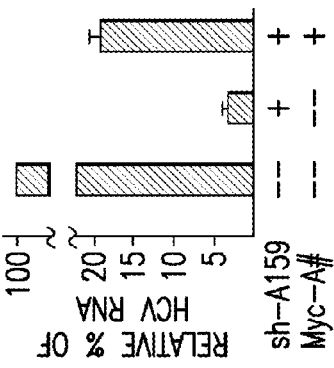

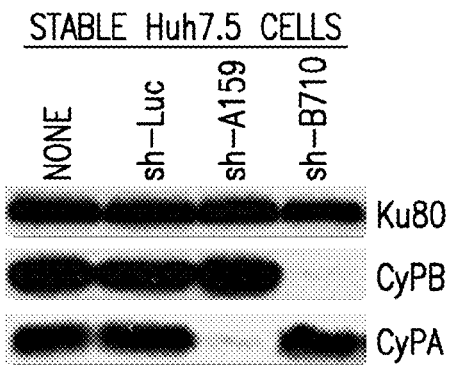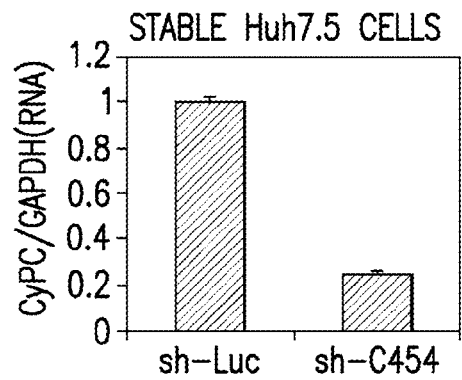
FIG.4A
FIG.4B
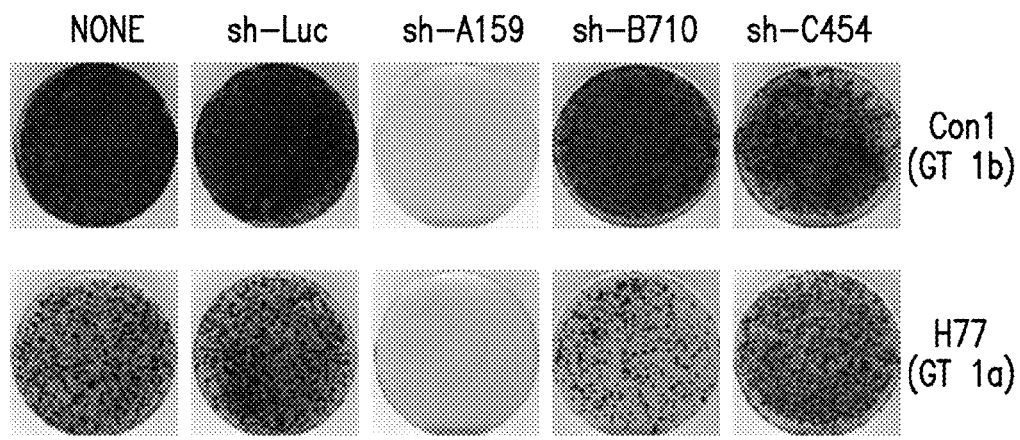
FIG.4C
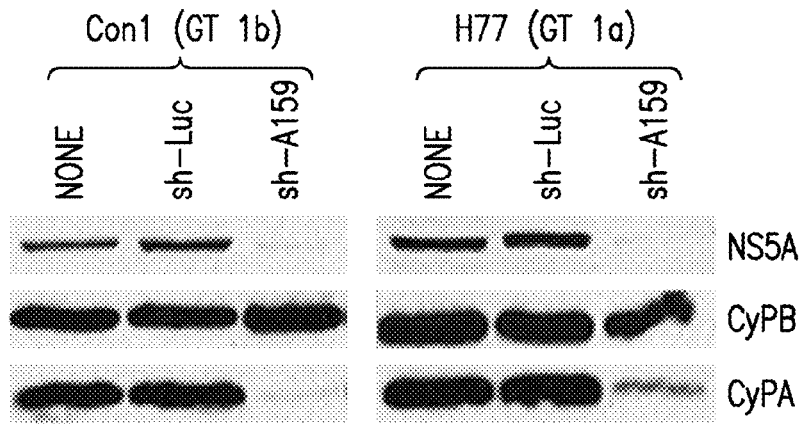
FIG.4D

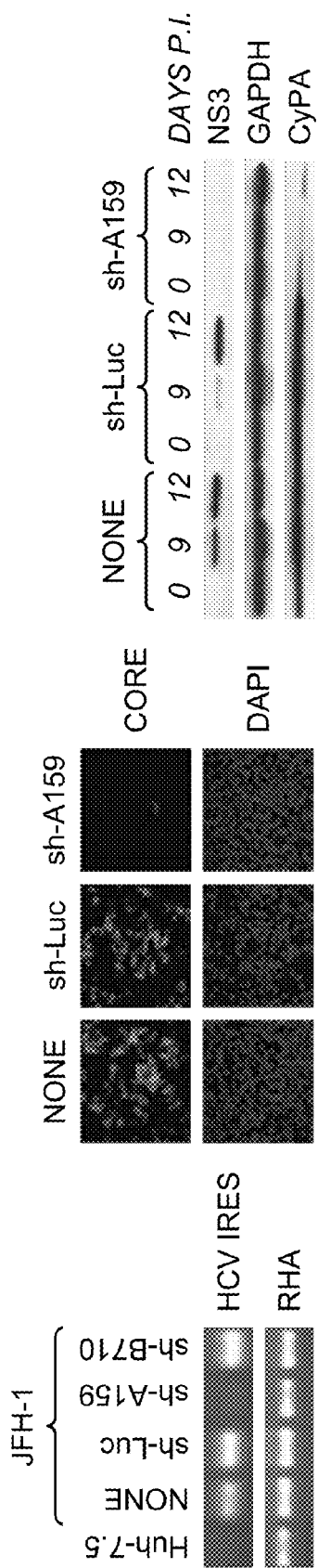
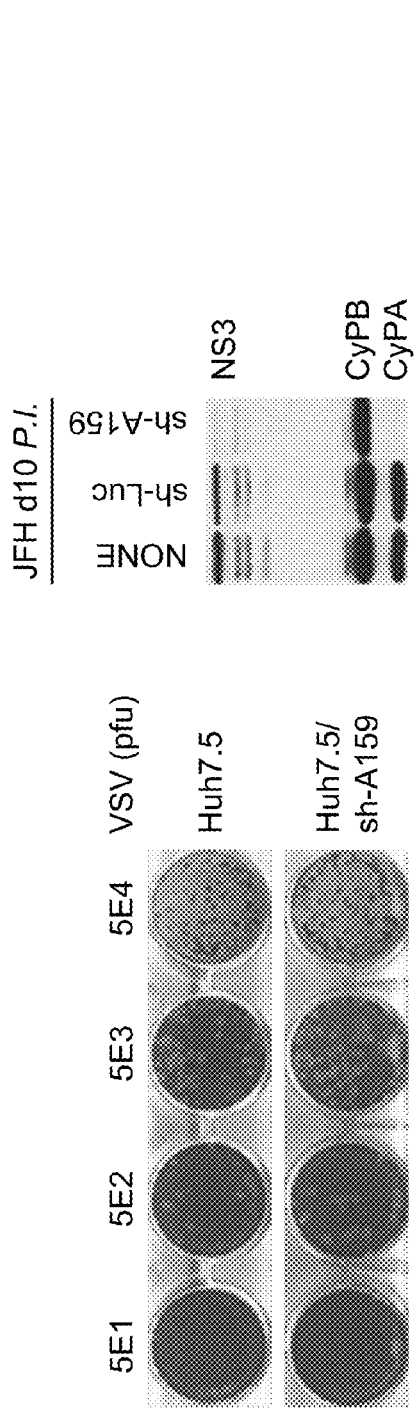
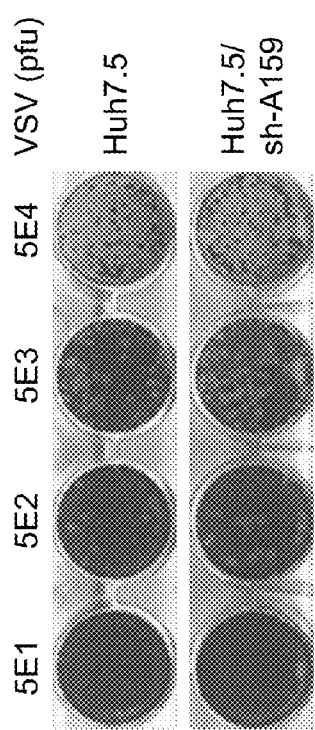

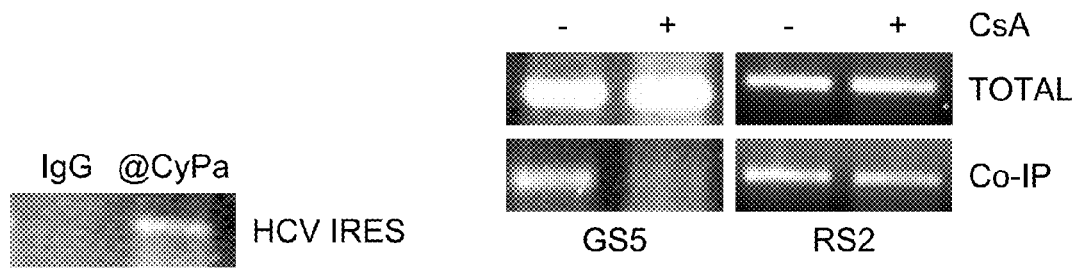
FIG.6A
FIG.6B
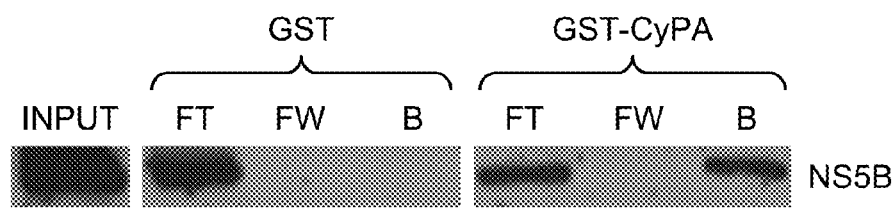
FIG.6C
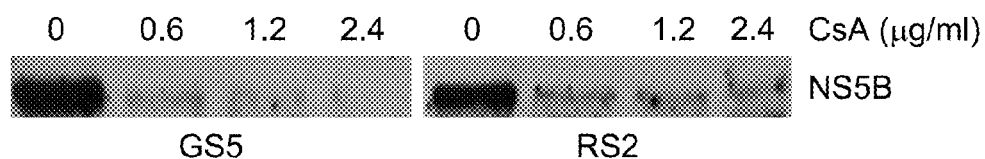
FIG.6D
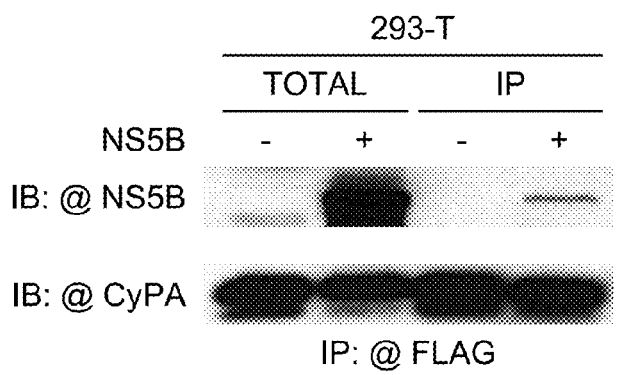
FIG.6E

RNAI THERAPEUTIC FOR TREATMENT OF HEPATITIS C INFECTION

CROSS-REFERENCE TO RELATED APPLICATIONS

This application is a divisional of U.S. patent application Ser. No. 13/034,851, filed Feb. 25, 2011, allowed, which is a divisional of U.S. Pat. No. 7,910,722, issued Mar. 22, 2011, which claims the priority date from U.S. Prov. App. No. 60/948,040, entitled "NOVEL RNAi THERAPEUTIC FOR TREATMENT OF HEPATITIS C INFECTION," filed Jul. 5, 2007, and the entire disclosure and contents of this provisional application are hereby incorporated by reference. This application also makes reference to U.S. patent application Ser. No. 13/558,428, pending, filed Jul. 26, 2012 and U.S. Pat. No. 8,252,763, issued, Aug. 28, 2012, entitled the same.

GOVERNMENT INTEREST STATEMENT

This invention was made with support from the State of Florida under Florida Department of Health Grant No. 06NIR. The State of Florida may have rights to this invention.

BACKGROUND

1. Field of the Invention

The present invention relates generally to compositions comprising small interfering RNA (siRNA) or small hairpin RNA (shRNA) sequences corresponding to at least a portion of cyclophilin A (CyPA) to treat, manage, inhibit, or prevent, etc., viral infection by hepatitis C virus (HCV) in a host. The present invention further generally relates to methods of treating, managing, inhibiting, preventing, etc., HCV using such compositions.

2. Background of the Invention

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. HCV, a member of the Flaviviridae family that includes other major human pathogens such as dengue and West Nile viruses, contains a positive-strand RNA genome of 9.6 kb encoding a single polyprotein, which is processed through proteolysis to become at least 10 viral proteins. See, e.g., Lindenbach, B. D. et al., "Unraveling hepatitis C virus replication from genome to function," *Nature* 436:933-938 (2005), the entire disclosure and contents of which is hereby incorporated by reference.

RNA interference ("RNAi") refers to the process of sequence-specific post-transcriptional gene silencing in animals mediated by short interfering RNAs (siRNAs). See, Fire et al., *Nature*, 391:806 (1998). The corresponding process in plants is commonly referred to as post-transcriptional gene silencing or RNA silencing and may also be referred to as quelling in fungi. The process of post-transcriptional gene silencing is thought to be an evolutionarily-conserved cellular defense mechanism used to prevent the expression of foreign genes and is commonly shared by diverse flora and phyla. See, Fire et al., "RNA-triggered gene silencing," *Trends Genet.* 15(9):358-63 (1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The process of RNAi begins by the presence of dsRNA in a cell, wherein the dsRNA comprises a sense RNA having a sequence homologous to the target gene mRNA and an antisense RNA having a sequence complementary to the sense RNA. In general, the presence of dsRNA stimulates the activity of a ribonuclease III enzyme referred to as Dicer. Dicer is involved in the processing of the dsRNA into short pieces of dsRNA known as short interfering RNAs (siRNAs). See, e.g., Bernstein et al., "Role for a bidentate ribonuclease in the initiation step of RNA interference," *Nature,* 409: 363 (2001). Short interfering RNAs derived from Dicer activity are typically about 21 to about 23 nucleotides in length and comprise about 19 base pair duplexes. See, e.g., Elbashir, S. M. et al., "RNA interference is mediated by 21- and 22-nucleotide RNAs," *Genes Dev.* 15:188 (2001). The siRNAs in turn stimulate the RNA-induced silencing complex (RISC) by incorporating one strand of siRNA into the RISC and directing the degradation of the homologous mRNA target.

SUMMARY

According to a first broad aspect of the present invention, there is provided a small interfering RNA (siRNA) comprising a sense RNA sequence and an antisense RNA sequence, wherein the sense RNA sequence is at least about 70% homologous to at least 19 contiguous nucleotides between nucleotides 155 and 183 of human cyclophilin A sequence (SEQ ID NO: 1) and wherein the antisense RNA sequence is complementary to the sense RNA sequence.

According to a second broad aspect of the present invention, there is provided a siRNA comprising a sense RNA sequence and an antisense RNA sequence, wherein the antisense RNA sequence is at least about 70% complementary to at least 19 contiguous nucleotides between nucleotides 155 and 183 of human cyclophilin A sequence (SEQ ID NO: 1) and wherein the sense RNA sequence is complementary to the antisense RNA sequence.

According to a third broad aspect of the present invention, there is provided a DNA polynucleotide comprising a DNA sequence region encoding a sense RNA sequence that is at least about 70% homologous to at least 19 contiguous nucleotides between nucleotides 155 and 183 of human cyclophilin A sequence (SEQ ID NO: 1).

According to a fourth broad aspect of the present invention, there is provided a DNA polynucleotide comprising a DNA sequence region encoding an antisense RNA sequence that is at least about 70% complementary to at least 19 contiguous nucleotides between nucleotides 155 and 183 of human cyclophilin A sequence (SEQ ID NO: 1).

According to a fifth broad aspect of the present invention, there is provided a method for inhibiting Hepatitis C virus (HCV) infection, comprising the following steps: (i) administering at least one siRNA comprising a sense RNA sequence and an antisense RNA sequence to an individual infected or at risk of infection with HCV, and (ii) monitoring the level of HCV infection, wherein the sense RNA sequence is at least 70% homologous to at least 19 contiguous nucleotides between nucleotides 155 and 183 of human cyclophilin A sequence (SEQ ID NO: 1) and wherein the antisense RNA sequence is complementary to the sense RNA sequence.

According to a sixth broad aspect of the present invention, there is provided a method for inhibiting Hepatitis C virus (HCV) infection comprising the following steps: (i) administering at least one small hairpin RNA (shRNA) comprising a sense RNA sequence and an antisense RNA sequence covalently linked by a hairpin sequence to an individual infected or at risk of infection with HCV, and (ii) monitoring the level of HCV infection, wherein the sense RNA sequence is at least about 70% homologous to at least 19 contiguous nucleotides between nucleotides 155 and 183 of human cyclophilin A sequence (SEQ ID NO: 1) and wherein the antisense RNA sequence is complementary to the sense RNA sequence.

According to a seventh broad aspect of the present invention, there is provided a method for inhibiting Hepatitis C virus (HCV) infection comprising the following steps: (i) administering at least one DNA polynucleotide comprising a DNA sequence region encoding a sense RNA sequence to an individual infected or at risk of infection with HCV, and (ii) monitoring the level of HCV infection, wherein the sense RNA sequence is at least about 70% homologous to at least 19 contiguous nucleotides between nucleotides 155 and 183 of human cyclophilin A sequence (SEQ ID NO: 1).

BRIEF DESCRIPTION OF THE DRAWINGS

The invention will be described in conjunction with the accompanying drawings, in which:

FIG. 2A is a schematic representation of the target sites of various shRNAs (A159, A285, A285', and A459) in CyPA, as well as target sites of previously reported siRNAs, with example target sequence for each shown as antisense RNA sequences (A159 (SEQ ID NO. 4), A285 (SEQ ID NO. 20), A285' (SEQ ID NO. 21), and A459 (SEQ ID NO. 22));

FIG. 2B is an image of Western blots showing expression of the proteins NS5A, Actin, and CyPA in GS5 cells transduced with various shRNAs (sh-Luc, sh-A159, sh-A285, sh-A459, sh-NTC, or sh-A285') for 7 days prior to lysis;

FIG. 2C is an image of Western blots showing expression of the indicated proteins (NS5A, Actin, and CyPA) in GS5 cells seven days after transfection with siRNA duplexes (si-NTC, si-A159, or si-285);

FIG. 2D is an image of Western blots showing expression of the proteins NS5A, Actin, and Myc-tagged CyPA in GS5 cells transduced with sh-Luc or sh-A159, with or without transfection of a Myc-tagged CyPA cDNA (Myc-A#) containing silent mutations in the recognition site of sh-A159;

FIG. 2E is a bar graph showing relative HCV RNA expressed as a ratio of HCV RNA extracted at day 4 to HCV RNA extracted at 7 hours after co-electroporation of in vitro transcribed Rep1b RNA into CyPA-knock-down Huh-7.5 cells, with or without expression from a CyPA# cDNA (Myc-A#) plasmid, with HCV RNA measured as a normalized level of HCV IRES to GAPDH RNA. A parallel electroporation of Rep1b RNA into Huh-7.5/sh-Luc cells serves as a positive control, which is set at 100%;

FIG. 4A is an image of a Western blot showing expression of the proteins Ku80, CyPB, and CyPA in Huh-7.5 cells transduced with several shRNAs (sh-Luc, sh-A159, or sh-B710);

FIG. 4B is a bar graph showing normalized levels of CyPC RNA to GAPDH RNA in Huh-7.5 cells transduced with indicated shRNAs (sh-Luc or sh-C454);

FIG. 4C is an image of plates containing stained Huh-7.5 cells transduced with several shRNAs (sh-Luc, sh-A159, sh-B710, or sh-C454) after four weeks following electroporation with one microgram of either H77 (GT 1a) or Con1 (GT 1b) replicons;

FIG. 4D is an image of Western blots showing expression of the proteins NS5A, CyPB, and CyPA in H77 (GT 1a) and Con1 (GT 1b) replicon cells transduced with the indicated shRNAs (sh-Luc or sh-A161);

FIG. 5A is an image of an RNA gel showing HCV IRES RNA levels relative to cellular RNA helicase A (RHA) RNA in total RNA extracts from Huh7.5 cells transduced with several shRNAs (sh-Luc, sh-A159, or sh-B710) following infection with HCVcc/JFH-1 for nine days;

FIG. 5B is a fluorescence microscopy image showing anti-core antibody and DAPI (4',6'-diamidino-2-phenylindole) staining of paraformaldehyde fixed Huh7.5 cells transduced with either sh-Luc or sh-A159 following infection with HCVcc/JFH-1 for nine days;

FIG. 5C is an image of Western blots showing expression of the proteins NS3, GAPDH, and CyPA in total protein extracts from Huh7.5 cells transduced with the indicated shRNAs (sh-Luc or sh-A159) at 0, 9, or 12 days after infection with HCVcc/JFH-1 replicons;

FIG. 5D is an image of infection plaques formed by vesicular stomatitis virus (VSV) in plates containing Huh7.5 cells, with or without transduction with sh-A159, and subjected to serial dilutions of 50 to $5 \times 10^4$ PFU of VSV;

FIG. 5E is an image of a Western blot showing expression of the proteins NS3, CyPB, and CyPA in total protein extracts from Huh-7.5 cells ten days after transduction with the indicated shRNAs (sh-Luc or sh-A159) with the indicated transduction occurring after infection with HCVcc/JFH-1 for ten days;

FIG. 6A is an image of an RNA gel showing HCV IRES RNA from GS5 replicon cells co-precipitated with an antibody for CyPA or control IgG as detected by RT-PCR;

FIG. 6B is an image of an RNA gel showing presence of HCV IRES RNA in total RNA from GS5 and RS2 replicon cells and RNA from GS5 and RS2 replicon cells co-precipitated with an antibody for CyPA in the presence or absence of 4 μg/ml CsA;

FIG. 6C is an image of a Western blot showing presence of NS5B protein in samples from GS5 replicon lysates incubated with equal amounts of GST or GST-CyPA and purified with glutathione beads (FT=flowthrough; FW=final wash; and B=bound);

FIG. 6D is an image of a Western blot showing presence of NS5B in samples using the GST pull-down assay from FIG. 6C on lysates from GS5 or RS2 cells in the presence of increasing amounts of CsA;

FIG. 6E is an image of a Western blot showing presence of NS5B and CyPA in total cell lysates from 293-T cells or samples produced by immunoprecipitation with anti-Flag antibody of lysates from 293-T cells following co-transfection of 293-T cells with plasmids expressing Flag-tagged CyPA, with or without plasmids expressing Con1 NS5B for 48 hours;

BRIEF DESCRIPTION OF SEQUENCE LISTINGS

Figure 1A:
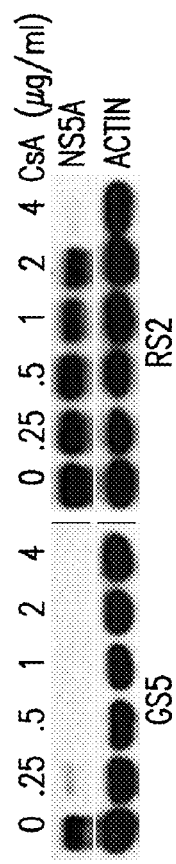
FIG. 1A. is an image of Western blots showing expression of the proteins NS5A and Actin in GS5 and RS2 replicon cells after being treated with CsA at various concentrations for 4 days.

SEQ ID NO: 1 (CyPA cDNA clone Y00052) shows the nucleotide sequence of human cyclophilin A cDNA as provided by accession number Y00052 or as follows:

GTGTACTATTAGCCATGGTCAACCCCACCGTGTTCTTCGACATTGCCGTC

GACGGCGAGCCCTTGGGCCGCGTCTCCTTTGAGCTGTTTGCAGACAAGGT

CCCAAAGACAGCAGAAAATTTTCGTGCTCTGAGCACTGGAGAGAAAGGAT

TTGGTTATAAGGGTTCCTGCTTTCACAGAATTATTCCAGGGTTTATGTGT

CAGGGTGGTGACTTCACACGCCATAATGGCACTGGTGGCAAGTCCATCTA

TGGGGAGAAATTTGAAGATGAGAACTTCATCCTAAAGCATACGGGTCCTG

GCATCTTGTCCATGGCAAATGCTGGACCCAACACAAATGGTTCCCAGTTT

TTCATCTGCACTGCCAAGACTGAGTGGTTGGATGGCAAGCATGTGGTGTT

TGGCAAAGTGAAAGAAGGCATGAATATTGTGGAGGCCATGGAGCGCTTTG

GGTCCAGGAATGGCAAGACCAGCAAGAAGATCACCATTGCTGACTGTGGA

CAACTCGAATAAGTTTGACTTGTGTTTTATCTTAACCACCAGATCATTCC

TTCTGTAGCTCAGGAGAGCACCCCTCCACCCCATTTGCTCGCAGTATCCT

AGAATCTTTGTGCTCTCGCTGCAGTTCCCTTTGGGTTCCATGTTTTCCTT

GTTCCCTCCCATGCCTAGCTGGATTGCAGAGTTAAGTTTATGATTATGAA

ATAAAAACTAAATAACAATTGTC;

SEQ ID NO: 2 (sense A-159) shows an example of a sense RNA sequence used in embodiments of the present invention corresponding to nucleotides 159 through 179 of human CyPA cDNA and is as follows: 5'-AAG GGU UCC UGC UUU CAC AGA-3';

SEQ ID NO: 3 (sh-A159) shows an example of a shRNA sequence used in embodiments of the present invention corresponding to a sense sequence having nucleotides 159 through 179 of CyPA cDNA and is as follows: 5'-AAG GGU UCC UGC UUU CAC AGA UUC AAG AGA UCU GUG AAA GCA GGA ACC CUU-3';

SEQ ID NO: 4 (antisense A-159) shows an example of an antisense RNA sequence used in embodiments of the present invention complementary to a sequence corresponding to nucleotides 159 through 179 of human CyPA cDNA and is as follows: 5'-UCU GUG AAA GCA GGA ACC CUU-3';

SEQ ID NO: 5 (sh-A159 DNA template) shows an example of a minimal DNA template for expression of a shRNA used in embodiments of the present invention and is as follows: 5'-TTC CCA AGG ACG AAA GTG TCT AAG TTC TCT AGA CAC TTT CGT CCT TGG GAA-3';

SEQ ID NO: 6 (A-159) shows a sense DNA sequence for a siRNA or shRNA and is as follows: 5'-AAG GGT TCC TGC TTT CAC AGA-3';

SEQ ID NO: 7 (A-285) shows a sense DNA sequence for a siRNA or shRNA and is as follows: 5'-AAG CAT ACG GGT CCT GGC ATC-3';

SEQ ID NO: 8 (A-285') shows a sense DNA sequence for a siRNA or shRNA and is as follows: 5'-AAG CAT ACA GGT CCT GGC ATC-3';

SEQ ID NO: 9 (A-459) shows a sense DNA sequence for a siRNA or shRNA and is as follows: 5'-AAT GGC AAG ACC AGC AAG AAG-3';

SEQ ID NO: 10 (C-454) shows a sense DNA sequence for a siRNA or shRNA corresponding to nucleotides 454 through 474 of CyPC cDNA (Accession number 571018) and is as follows: 5'-AAG ACT GAA GGT GTG CTG GTA-3';

SEQ ID NO: 11 (NTC) shows a "no target control" DNA sequence for a siRNA or shRNA that does not have a target in the human genome and is as follows: 5'-AAG GAG GTG ACA TCA CCA CTG-3';

SEQ ID NO: 12 (A-forward) is a forward primer for CyPA and is as follows: 5'-CGG GTC CTG GCA TCT TGT-3';

SEQ ID NO: 13 (A-reverse) is a reverse primer for CyPA and is as follows: 5'-GCA GAT GAA AAA CTG GGA ACCA-3';

SEQ ID NO: 14 (B-forward) is a forward primer for CyPB and is as follows: 5'-GGC CAA CGC AGG CAA A-3';

SEQ ID NO: 15 (B-reverse) is a reverse primer for CyPB and is as follows: 5'-TCT AGC CAG GCT GTC TTG ACT GT-3';

SEQ ID NO: 16 (C-forward) is a forward primer for CyPC and is as follows: 5'-GCT GAA GCA CTA TGG CAT TGG-3';

SEQ ID NO: 17 (C-reverse) is a reverse primer for CyPC and is as follows: 5'-GAA CTG AGA GCC ATT GGT GTC A-3';

SEQ ID NO: 18 (IRES forward) is a forward primer for HCV internal ribosome entry site (IRES) and is as follows: 5'-GTC TGC GGA ACC GGT GAG-3';

SEQ ID NO: 19 (IRES reverse) is a reverse primer for HCV internal ribosome entry site (IRES) and is as follows: 5'-CGG GTT GAT CCA AGA AAG GAC-3';

SEQ ID NO: 20 (antisense A-285) shows an antisense RNA sequence corresponding to a target sequence for a siRNA or shRNA and is as follows: 5'-GAU GCC AGG ACC CGU AUG CUU-3';

SEQ ID NO: 21 (antisense A-285') shows an antisense RNA sequence corresponding to a target sequence for a siRNA or shRNA and is as follows: 5'-GAU GCC AGG ACC UGU AUG CUU-3'; and SEQ ID NO: 22 (antisense A-459) shows an antisense RNA sequence corresponding to a target sequence for a siRNA or shRNA and is as follows: 5'-CUU CUU GCU GGU CUU GCC AUU-3'.

DETAILED DESCRIPTION

Definitions

The definition of terms departs from the commonly used meaning of the term, applicant intends to utilize the definitions provided below, unless specifically indicated.

For the purposes of the present invention, the term "comprising" means various compositions, molecules, genes, polypeptides (proteins), polynucleotides, plasmids, vectors, components, capabilities and/or steps, etc., can be conjointly employed in embodiments of the present invention. Accordingly, the term "comprising" encompasses the more restrictive terms "consisting essentially of" and "consisting of"

For the purposes of the present invention, the term "complementary" or "complementarity" refers to polynucleotides that are able to form base pairs with one another. Base pairs are typically formed by hydrogen bonds between nucleotide units in an anti-parallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present invention, the ability to substitute a thymine is implied, unless otherwise stated. "Complementarity" may exist between two RNA strands, two DNA strands, or between a RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art. For purposes of RNAi, sense and antisense strands of a siRNA or sense and antisense sequences of a shRNA composition may be deemed "complementary" if they have sufficient base-pairing to form a duplex (i.e., they hybridize with each other at a physiological temperature).

For the purposes of the present invention, the term "polynucleotide" may refer to either (i) a single-stranded DNA or RNA molecule or sequence, or a modified version thereof, or (ii) double-stranded DNA and/or RNA molecules, sequences, or hybrids, or modified version(s) thereof. For example, the term "polynucleotide" may refer to any double-stranded polynucleotide encoding a sense RNA sequence and an antisense RNA sequence wherein such polynucleotide sequences encoding the sense and antisense RNA sequences being directly base paired with each other.

For the purposes of the present invention, the terms "encode," "encodes," or "encoding" refer to the ability of an originating polynucleotide to be transcribed, reverse transcribed, expressed, replicated, and/or translated into the same or different polynucleotide and/or polypeptide product, as the case may be. Such polynucleotide and/or polypeptide product is described as being "encoded by" such originating polynucleotide. Likewise, viral vectors may be described as "encoding" a polynucleotide or polypeptide product by containing such originating polynucleotide within its genome in accordance with its genome type, such as single- or double-stranded DNA or RNA, as the case may be.

For the purposes of the present invention, the term "expression vector" refers to both viral and non-viral vectors comprising a nucleic acid expression cassette.

For the purposes of the present invention, the term "expression cassette" is used to define a nucleotide sequence containing regulatory elements operably linked to a coding sequence, such that the product of the coding sequence is expressed in a cell in a regulated or a constitutive manner.

For the purposes of the present invention, the term "gene" refers to a nucleic acid (e.g., DNA) sequence that comprises coding sequences necessary for the production of mRNA or polypeptide molecules or other RNA molecules (e.g., tRNA, rRNA, etc.). However, the term gene may further refer to the template strand for a gene. A functional polypeptide may be encoded by a full length coding sequence or by any portion of the coding sequence of a gene so long as the desired activity or functional properties (e.g., enzymatic activity, ligand binding, signal transduction, etc.) of the full-length protein or fragment are retained. The term "gene" may also encompass sequences located adjacent to the coding region on both the 5' and 3' ends in addition to the coding region of a structural gene, such that the concept of the "gene" includes other portions of the full-length mRNA, such as 5' and 3' untranslated regions (UTRs). The term "gene" may also encompass both cDNA and genomic sequences of a gene, and portions thereof. Such genomic sequences for a gene may further contain non-coding sequences termed "introns" or "intervening regions" or "intervening sequences," which may interrupt the coding regions of a gene, termed "exons." Such introns are spliced out of the mature mRNA sequence that is used to encode the protein product of a gene.

For the purposes of the present invention, the term "template strand" generally refers to a DNA sequence of a gene complementary to all or apportion of a mRNA sequence expressed from such gene keeping in mind differences between DNA and RNA sequences, such uracil in place of thymine in RNA sequences, and vice versa.

For the purposes of the present invention, the term "coding strand" refers to a DNA sequence of a gene corresponding directly to all or a portion of a mRNA sequence expressed from such gene keeping in mind differences between DNA and RNA sequences.

For the purposes of the present invention, the term "hepatitis C virus (HCV)" refers to the ordinary meaning of this term in the art. The hepatitis C virus is an RNA virus of the Flaviviridae family. The terms "Hepatitis C virus" or "HCV" may include, without limitation, any previously identified genotype of HCV, such as genotypes 1-11 (using the most common genotyping system), which may be broken down into various subtypes including, without limitation, 1a, 1b, 1c, 2a, 2b, 2c, 3a, 3b, 4a, 4b, 4c, 4d, 4e, 5a, 6a, 7a, 7b, 8a, 8b, 9a, 10a and 11a. Further, the terms "Hepatitis C virus" or "HCV" may include isolates taken from individuals comprising or consisting of closely related, yet heterogeneous, populations of viral genomes, sometimes referred to as quasispecies. In addition, the terms "Hepatitis C virus" or "HCV" may include genotypes that would be understood as being HCV or sufficiently resembling HCV to be labeled or categorized as such that have not yet emerged or been identified.

For the purposes of the present invention, the terms "homology" or "homologous" when used in the context of nucleic acid or polypeptide sequences refer to sequence identity or similarity between two or more sequences. The degree of sequence identity is generally quantified using percentages, which is calculated based on the number of differing nucleotides or amino acids over the total length of the sequence. Determining the percentage of homology is a matter of skill in the art. For example, sequence alignment programs may be used to aid the determination of the degree of identity or homology between two or more sequences. Homologous sequences may comprise two or more DNA sequences, two or more RNA sequences, or at least one DNA sequence and at least one RNA sequence. When comparing DNA and RNA sequences, it is generally understood that a uracil (U) in a RNA sequence is considered equivalent to a thymine (T) in a DNA sequence for purposes of determining homology.

For the purposes of the present invention, the term "small interfering RNA" or "siRNA" refers to double-stranded RNA molecules, comprising a sense strand and an antisense strand, having sufficient complementarity to one another to form a duplex. Such sense and antisense strands each have a region of complementarity ranging, for example, from about 10 to about 30 contiguous nucleotides that base pair sufficiently to form a duplex or double-stranded siRNA. Such siRNAs are able to specifically interfere with the expression of a gene by triggering the RNAi machinery of a cell to remove RNA transcripts having identical or homologous sequences to the siRNA sequence. As described herein, the sense and antisense strands of siRNA may each consist of only complementary regions, or one or both strands may comprise additional sequences, including non-complementary sequences, such 5' and 3' overhangs. In addition, such siRNAs may have other modifications, such as, for example, substituted or engineered nucleotides or other sequences, which contribute to either the stability of the siRNA, its delivery to a cell or tissue, or its potency in triggering RNAi. It is to be understood that the terms "strand" and "oligonucleotide" may be used interchangeably in reference to the sense and antisense strands of siRNA compositions.

For the purposes of the present invention, the terms "patient," "subject," or "individual" as used herein may be used interchangeably and generally refer to any animal, preferably mammals, that may be infected or at risk of infection by HCV. Such terms may refer to any animal having domesticated, agricultural, commercial, or other research uses. The terms "patient," "subject," or "individual" may also refer to humans.

For the purposes of the present invention, the term "3' overhang" refers to at least one unpaired nucleotide extending out from the 3'-end of at least one strand of the duplexed siRNA and may engineered into an shRNA. Similarly, the term "5' overhang" refers to at least one unpaired nucleotide extending out from the 5'-end of at least one strand of the duplexed siRNA.

For the purposes of the present invention, the term "region" when applied to polynucleotides generally refers to a contiguous portion or sequence of a single-stranded or double-stranded polynucleotide molecule(s). However, the term "region" may also refer to an entire single-stranded or double-stranded polynucleotide molecule(s).

For the purposes of the present invention, the term "physiological conditions" refers to conditions that approximate the chemical and/or temperature environment that may exist within the body of an individual, subject, or patient.

For the purposes of the present invention, the term "physiological temperature" generally refers to a temperature present within the body of an individual, subject, or patient. The term "physiological temperature" may be assumed to be approximately 37° C. unless otherwise specified.

For the purposes of the present invention, the term "sense RNA" refers to a RNA sequence corresponding to all or a portion of a coding sequence of a gene or all or a portion of a plus (+) strand or mRNA sequence generated from a gene, or a RNA sequence homologous thereto, keeping in mind the differences between RNA and DNA molecules.

For the purposes of the present invention, the term "antisense RNA" refers to a RNA sequence corresponding to all or a portion of a template sequence of a gene, or a sequence homologous thereto, or a minus (−) strand or all or a portion of a sequence complementary to a mRNA sequence generated from a gene, keeping in mind the differences between RNA and DNA molecules.

For the purposes of the present invention, the term "hybridize" refers to associating two complementary nucleic acid strands to form a double-stranded molecule which may contain two DNA strands, two RNA strands, one DNA and one RNA strand, etc.

Relative to U.S. Provisional App. No. 60/948,040, sequence ranges and nucleotide numbers within CyPA cDNA have been updated herein to more consistently match cDNA sequences as provided by accession number Y00052 and SEQ ID NO: 1. For example, the nucleotide sequence range 157 to 185 referred to in U.S. Provisional App. No. 60/948,040 has been correspondingly updated herein to nucleotides 155 to 183, nucleotide sequence range 161 to 181 referred to in U.S. Provisional App. No. 60/948,040 has been correspondingly updated herein to nucleotides 159 to 179, and A161 and sh-A161 referred to in U.S. Provisional App. No. 60/948,040 have been correspondingly renamed as A159 and sh-A159, respectively. Unless otherwise stated, these sequence ranges and nucleotide numbers referred to herein are the updated or renamed ranges and numbers.

Description

RNAi, as originally discovered in invertebrates and employed dsRNAs with length greater than 30 nucleotides, is not effective in mammalian cells. This was found to be due to the fact that long dsRNAs (greater than 30 nucleotides) elicit interferon responses, resulting in nonspecific mRNA degradation and inhibition of protein synthesis. This problem may be overcome by using smaller double-stranded siRNAs, e.g. 20-23 nucleotides in length for each strand, which do not induce an interferon response yet remain potent and specific inhibitors of endogenous gene expression. See, e.g., Elbashir, S. M. et al., "RNA interference is mediated by 21- and 22-nucleotide RNAs," *Genes Dev.* 15:188 (2001).

In research laboratories, two types of siRNA (or shRNA) have been widely used to suppress exogenous as well as endogenous gene expression: synthetic siRNA and vector-based siRNA (i.e., in vivo transcribed siRNA). Synthetic siRNAs are generally synthesized in vitro prior to administration to cells; however, vector-based siRNAs are expressed from vectors introduced into cells. The vector-based approach is often carried out using short or small hairpin RNAs (shRNAs). Vector-based approaches may use RNA polymerase III promoters, such as H1 promoter and U6 promoter to drive transcription of a shRNA. The shRNA transcript may consist of a 19- to 29-bp RNA stem, with the two complementary (sense and antisense) strands joined by a tightly structured hairpin or loop. The shRNA may be processed in the cell into siRNA through the action of the Dicer family of enzymes. Thus, the transcribed products may mimic the synthetic siRNA duplexes and may be as effective as the synthetic siRNA for suppressing their corresponding genes.

Previously, the most effective HCV therapy employed a combination of alpha-interferon and ribavirin, leading to sustained efficacy in only 40% of patients. In addition, recent clinical results have also shown that combined interferon and cyclosporine A treatment may be more effective in treating patients with chronic hepatitis C than interferon monotherapy, which may suggest a role for cyclosporin A as a valid treatment option for HCV. See, e.g., Inoue, K. et al., "Combined interferon a2b and cyclosporine A in the treatment of chronic hepatitis C: controlled trial," *Journal of Gastroenterology* 38(6):567-72 (2003).

However, treatment of HCV infection has been met with less than satisfactory results primarily because of the resistance to interferon-a (IFN) and possible side effects of existing therapies. Most current efforts to develop new HCV drugs have focused on viral targets, such as inhibitors of viral protease and polymerase enzymes. However, resistance to these inhibitors readily develops in vitro and in vivo. New classes of safe and broadly-acting treatments are therefore urgently needed.

siRNAs targeting HCV are known. However, these siRNAs directly target the viral genome, which mutates rapidly. Thus, resistance to such siRNAs quickly develops when mutations at siRNA target sites arise. Therefore, a need for the development of novel compositions and methods for the treatment, maintenance, inhibition, prevention, etc., of HCV infection continues.

Cyclophilins (CyPs) are a family of cellular enzymes possessing the peptidyl-prolyl isomerase activity. The prototypical member of the CyP family is Cyclophilin A (CyPA), the main intracellular ligand of cyclosporine (CsA) (see, e.g., Handschumacher, R. E. et al., "Cyclophilin: a specific cytosolic binding protein for cyclosporine A," *Science* 226:544-547 (1984)), an immunosuppressant which is usually used to suppress rejection after internal organ transplants. CyPA exists in the cytosol and has a beta barrel structure with two alpha helices and a beta sheet. CyPA plays the role of a molecular chaperone, i.e., it helps other proteins fold correctly.

The role of human CyPs as cellular cofactors in HCV replication is suggested by studies that show that CsA is effective in suppressing HCV replication. See, e.g., Nakagawa, M., N. et al. Specific inhibition of hepatitis C virus replication by cyclosporin A," *Biochem. Biophys. Res. Commun.* 313:42-47 (2004); Watashi, K. et al., "Cyclosporin A suppresses replication of hepatitis C virus genome in cultured hepatocytes," *Hepatology* 38:1282-1288 (2003). Subsequently, a correlation between the CyP-binding and anti-HCV activity has been observed for derivatives of CsA. See, e.g., Ma, S. et al., "NIM811, a cyclophilin inhibitor, exhibits potent in vitro activity against hepatitis C virus alone or in combination with alpha interferon," *Antimicrob. Agents Chemother.* 50:2976-2982 (2006); Watashi, K. et al., "Cyclophilin B is a functional regulator of hepatitis C virus RNA polymerase," *Mol. Cell.* 19:111-122 (2005). But despite both protein binding and resistance mapping studies that might suggest that NS5B is a viral target for CsA (see, e.g., Fernandes, F. D. et al., "Sensitivity of hepatitis C virus to cyclosporine A depends on nonstructural proteins NS5A and NS5B," *Hepatology* 46:1026-1033 (2007); Robida, J. M. et al., "Characterization of hepatitis C virus subgenomic replicon resistance to cyclosporine in vitro" *J. Virol.* 81:5829-5840 (2007); Watashi, K. et al., "Cyclophilin B is a functional regulator of hepatitis C virus RNA polymerase," *Mol. Cell.* 19:111-122 (2005)), the identities and relative contributions of the various CyPs implicated in this interaction remain debatable (see, e.g., Nakagawa, M. et al., "Suppression of hepatitis C virus replication by cyclosporine a is mediated by blockade of cyclophilins," *Gastroenterology* 129:1031-1041 (2005); Robida, J. M. et al., "Characterization of hepatitis C virus subgenomic replicon resistance to cyclosporine in vitro. *J. Virol.* 81:5829-5840 (2007); Watashi, K. et al. Cyclophilin B is a functional regulator of hepatitis C virus RNA polymerase. *Mol. Cell.* 19:111-122 (2005)).

As described herein, it has been found that CyPA, and not CyPB or CyPC, is an essential cofactor for the replication of various HCV isolates and genotypes. Therefore, according to some embodiments of the present invention, compositions and methods are provided for the treatment and/or prevention of HCV infection in a cell or an individual, subject, or patient using an inhibitor of CyPA. More particularly, such compositions and methods may comprise siRNAs, shRNAs, or other RNAi-mediated compositions that specifically target CyPA to effectively inhibit, prevent, treat, and/or manage HCV infection and/or disease. Applicants describe herein that siRNA or shRNA compositions of the present invention that target a specific region of CyPA corresponding to at least 19 contiguous nucleotides from about nucleotide 155 to about nucleotide 183 of the coding sequence of human CyPA cDNA (accession number Y00052; SEQ ID NO: 1) are especially potent and effective at targeting and inhibiting CyPA as well as the production of HCV virions.

It has been further found herein that CyPA is the principal mediator of CsA resistance in vitro and that Cyclosporin A-resistant (CsA-resistant) HCV strains show less dependency on CyPA. However, depletion of CyPA from host cells by RNAi has also been found herein to sensitize CsA-resistant HCV to CsA treatment. According to some embodiments, siRNA, shRNA, or other RNAi-mediated compositions and methods according to embodiments of the present invention may specifically target CyPA and may be further used in combination with other drugs or therapies, such as interferon and/or CsA. Such combined therapies may have cumulative or synergistic effects in treating, managing, inhibiting, preventing, etc., HCV infection.

In general, siRNA molecules which are directed against viral targets, including Hepatitis C virus, may not provide a long-term cure or protection against the virus due to their ability of viruses, including HCV, to mutate quickly, and therefore avoid recognition by siRNAs. In contrast, the embodiments of the present invention may provide siRNA or shRNA compositions that specifically target a cellular gene, i.e., CyPA, thus encoding a protein necessary for reproduction of HCV in host cells. Since such a target gene is present within the host cell genome, it may not be subject to rapid mutational changes that occur with many viral targets.

Among the various embodiments of the present invention is a small interfering RNA (siRNA) comprising a sense RNA sequence and an antisense RNA sequence which form an RNA duplex, wherein the sense RNA sequence is at least about 70% homologous to at least 19 contiguous nucleotides from nucleotide 155 to nucleotide 183 of human cyclophilin A cDNA sequence (with accession number Y00052; SEQ ID NO: 1) and wherein the antisense RNA sequence is complementary thereto. However, the degree of homology between sense RNA sequence of siRNA and at least 19 contiguous nucleotides of CyPA between nucleotides 155 and 183 of the coding sequence of CyPA cDNA may be higher, such as, for example, at least about 80%, 90%, 95%, or 100% homologous or identical, with antisense RNA sequence complementary thereto.

Described a different way, the antisense RNA sequence of siRNA of embodiments of the present invention may be at least about 70% complementary to at least 19 contiguous nucleotides between nucleotide 155 and nucleotide 183 of the coding sequence of human cyclophilin A cDNA (accession number Y00052) with sense RNA sequence complementary to such antisense RNA sequence or able to hybridize to the sense RNA sequence under physiological conditions. However, the degree of complementarity between antisense strand of siRNA and at least 19 contiguous nucleotides of CyPA between nucleotides 155 and 183 of the coding sequence of CyPA cDNA may be higher, such as, for example, at least about 80%, 90%, 95%, or 100% complementary, with a sense RNA sequence complementary thereto or able to hybridize thereto.

Alternatively, the sense and antisense RNA strands of siRNAs may be expressed as a single transcript, such that the sense and antisense RNA are covalently linked by a hairpin or stem-loop sequence to form a shRNA. Such shRNA may be cleaved when introduced into or expressed by a cell to yield two separate strands similar to the siRNA.

Embodiments of compositions of the present invention may further include any DNA polynucleotide sequences that encode any of the embodiments of the sense and/or antisense RNA sequences or strands of the present invention as described herein. Such DNA sequences may be placed into vectors, such as plasmids, viral vectors, etc., to achieve expression of the desired siRNA or shRNA. Expression from such vectors may be controlled using promoters known or used in the art.

According to some embodiments of the present invention, siRNA and shRNA compositions may be formulated as a pharmaceutical composition with a pharmaceutically acceptable carrier or in combination with delivery agents known in the art. Such siRNA and/or shRNA compositions may comprise two or more siRNAs and/or shRNAs having distinct sequences. Furthermore, such siRNA and/or shRNAs compositions may be used in combination with other known therapies or drugs.

In other embodiments of the present invention, methods for inhibiting hepatitis C virus replication and/or infection are provided, wherein such methods comprise introducing into a cell or tissue an siRNA or shRNA composition according to embodiments of the present invention (as described herein) that targets CyPA to inhibit HCV infection. Such methods for inhibiting HCV may be used to treat, manage, inhibit, prevent, etc., HCV infection in an individual, subject, or patient infected or at risk of infection by HCV and may be performed in combination with other therapies or drugs.

siRNA and shRNA Characteristics

According to some embodiments of the present invention, a small interfering RNA (siRNA) composition is provided, comprising a sense RNA sequence and an antisense RNA sequence corresponding to a region of CyPA, which has been shown to be involved in HCV infection. Thus, by introducing such siRNA composition into a cell, the level, expression, and/or activity of CyPA is reduced via RNAi and HCV infection is inhibited. According to one set of embodiments, for example, a sense RNA sequence (or strand) of siRNA of the present invention is at least about 70% homologous to at least 19 contiguous nucleotides between nucleotide 155 and nucleotide 183 of the coding sequence of human cyclophilin A cDNA (with accession number Y00052; SEQ ID NO: 1) with antisense RNA sequence (or strand) complementary to such sense RNA sequence (i.e., able to hybridize to the sense RNA sequence at a physiological temperature). However, the degree of homology between sense RNA sequence of siRNA and the at least 19 contiguous nucleotides of CyPA between nucleotides 155 and 183 of the coding sequence of CyPA cDNA may be higher, such as, for example, at least about 80%, 90%, 95%, or 100% homologous or identical, with antisense RNA sequence complementary thereto. According to some embodiments, sense RNA strand of siRNA composition may comprise SEQ ID NO: 2 corresponding to nucleotides 159 through 179 of CyPA, with an antisense strand complementary thereto.

According to some embodiments of the present invention, the antisense RNA sequence of siRNA is at least about 70% complementary to at least 19 contiguous nucleotides between nucleotide 155 and nucleotide 183 of the coding sequence of human cyclophilin A cDNA (with accession number Y00052; SEQ ID NO: 1) with sense RNA sequence complementary to such antisense RNA sequence (i.e., able to hybridize to the sense RNA sequence at a physiological temperature). However, the degree of complementarity between an antisense strand of siRNA and at least 19 contiguous nucleotides of CyPA between nucleotides 155 and 183 of the coding sequence of CyPA cDNA may be higher, such as, for example, at least about 80%, 90%, 95%, or 100% complementary, with sense RNA sequence complementary thereto.

Other embodiments of compositions of the present invention may further include any DNA polynucleotide sequences that encode any of the sense and/or antisense siRNA sequences or strands or shRNA sequences according to embodiments of the present invention as described herein. As described in greater detail below, such DNA sequences may be placed into vectors, such as plasmids, viral vectors, etc., to achieve expression of the desired siRNA or shRNA. The sense and antisense RNA sequences may be expressed by the same vector or separately by different vectors. For example, where the sense and antisense RNA sequences are expressed by the same vector, two promoters may be placed in opposite orientations flanking the portion of the DNA polynucleotide encoding the sense RNA sequence and the antisense RNA sequence from opposing strands that are directly base-paired with one another. Alternatively, for example, the sense and antisense RNA sequences may be expressed from a DNA polynucleotide as a single RNA molecule, such as a shRNA, linked by a hairpin sequence inserted between them. Therefore, embodiments of the present invention may further include any DNA polynucleotide sequence that encodes a shRNA sequence having a sense RNA sequence and an antisense RNA sequence covalently linked by a hairpin RNA sequence. For example, DNA sequence encoding shRNA may comprise SEQ ID NO: 5.

The sense and antisense sequences of siRNA compositions according to embodiments of the present invention are at least partially complementary to each other to form a duplex that is sufficient to trigger RNAi-mediated degradation of its target. However, it is to be understood that the degree of homology between the sense and antisense strand sequences of the siRNA and the coding and template sequences of human cyclophilin A, respectively, may be different (i.e., the degree of complementarity between the sense and antisense strands of siRNA of the present invention may be less than 100% and still have sufficient base-pairing to form a duplex and elicit specific RNAi-mediated destruction of its target, such as CyPA). One skilled in the art may achieve a desired homology and/or complementarity by making substitutions in either or both of the sense and antisense strand sequences as discussed below. It should be noted, however, that off-targeting and non-specific binding of sense or antisense RNA sequences should be avoided as much as possible so that ideally only the target, such as CyPA, is noticeably affected. Therefore, the actual degree of freedom available to relax the amount of homology between sense sequence of siRNA or shRNA of present invention and its target sequence may be limited. It should also be noted that the degree of complementarity between sense and antisense strands of siRNA should be sufficient to form a duplex such that RNAi-mediated degradation of its target is triggered.

The region of human CyPA corresponding to nucleotides 155 through 183 of the coding sequence of human cyclophilin A cDNA is specifically identified and chosen herein due to its potency in downregulating human CyPA and inhibiting HCV infection in cells as described herein. However, it is to be understood that embodiments of siRNA and shRNA compositions of the present invention may conceivably include other previously unknown contiguous sequences of human CyPA, including sequences outside of nucleotides 155 through 183, which may be effective at reducing the level, expression, activity, etc., of CyPA and/or HCV infection when introduced into cells. Furthermore, embodiments of siRNA or shRNA compositions of the present invention may comprise combinations of two or more siRNAs and/or shRNAs including those according to embodiments of the present invention having distinct sequences.

As mentioned above, human cyclophilin A sequence is known and available through GenBank (accession number Y00052). One skilled in the art may readily determine the proper nucleotide numbering for CyPA, such as the region comprising nucleotides 155 through 183 of the human cyclophilin A cDNA sequence (SEQ ID NO: 1). However, the genomic or cDNA sequence of human cyclophilin A may also be identified by different accession numbers, clones, or other identifiers. Embodiments of siRNA or shRNA compositions of the present invention may include any siRNA or shRNA sequences homologous to a region of a cyclophilin A gene or homologue derived from any non-human animal species that may experience HCV infection. For example, a region corresponding to nucleotides 155 through 183 of the human cyclophilin A cDNA sequence may be identified and used. A person skilled in the art would know how to find previously identified CyPA gene or homologue sequences from other species through standard sequence searching techniques.

One skilled in the art may be able to determine the appropriate number and type of substitutions or modifications in either the sense or antisense siRNA or shRNA strands or sequences relative to coding and template sequences of target, respectively, such that sufficient homology and complementarity is afforded to maintain base-pairing and duplex formation between sense and antisense strands or sequences to cause RNAi-mediated degradation of a target, such as CyPA. When making any such substitutions, considerations such as where they are introduced and whether they are dispersed throughout the sequence or occur together may affect the efficacy of the siRNA. By way of example, it is known in the art that substitutions in the center of the molecule tend to affect the efficacy to a greater degree than the substitutions at either end of the molecule. Similarly, two or more contiguous substitutions tend to affect binding or hybridization of sense and antisense strands to a greater extent than two or more spaced-apart mutations. Accordingly, substitutions may be introduced such that there are regions of at least 3 contiguous unmutated nucleotides between each substitution. For example, there may be at least 4 unmutated contiguous nucleotides, e.g., at least 5 unmutated contiguous nucleotides between each substitution.

The following features are not required, but may be useful, when determining which substitutions might be desirable in choosing siRNA or shRNA sequences that improve efficacy for RNAi-mediated compositions according to embodiments of the present invention: (1) a G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand.

In addition, if a substitution might result in a siRNA or shRNA sequence having one or more of the following criteria, such sequence may be less likely to function successfully as a siRNA or shRNA: (1) a sequence comprising a stretch of 4 or more of the same base in a row; (2) a sequence comprising homopolymers of Gs; (3) a sequence comprising triple base motifs (e.g., GGG, CCC, AAA, or TTT); (4) a sequence comprising stretches of 7 or more G/Cs in a row; and (5) a sequence comprising direct repeats of 4 or more bases within the candidates resulting in internal fold-back structures. However, such sequences may still be evaluated for the ability to function as siRNA or shRNA molecules. For further discussion of design guidelines that may be useful in designing siRNA or shRNA sequences for compositions and methods according to embodiments of the present invention directed against CyPA, see, e.g., De Paula, D. et al., "Hydrophobization and bioconjugation for enhanced siRNA delivery and targeting. RNA," 13: 431-56 (2007); and Chen, Y. et al., "RNAi for Treating Hepatitis B Viral Infection" *Pharmaceutical Research* 25(1): 72-86 (2008), the entire disclosures and contents of which are hereby incorporated by reference.

Accordingly, one skilled in the art may be able to determine which substitutions might be appropriate in designing siRNA or shRNA compositions according to embodiments of the present invention that would more likely target CyPA effectively. Based on known rules and principles, a person skilled may be able to determine appropriate modifications to the sense and/or antisense strands of a CyPA siRNA or shRNA according to embodiments of the present invention, such that sufficient complementarity and/or homology is more likely maintained to elicit RNAi-mediated degradation of CyPA despite having less than 100% homology with CyPA and/or less than 100% complementarity between sense and antisense strands of the siRNA.

Furthermore, siRNA or shRNA polynucleotides may be chemically synthesized or modified, e.g., for purposes of reducing immunostimulatory effect of siRNA sequences, affecting the potency of RNAi, increasing stability of siRNA or shRNA molecules, targeting to specific cells or tissues, and/or strengthening hybridization between sense and antisense strands. This may employ any known nucleotide derivatives or methods known or available in the art. Knowledge relating to backbone modifications used with antisense ODNs may be readily adapted to develop new siRNA or shRNA technologies. For example, the chemically modified siRNA may comprise modified nucleotides including, but not limited to, 2'-O-Me nucleotides, 2'-O-allyl nucleotides, 2'-deoxy-2'-fluoro (2'-F) nucleotides, 2'deoxy nucleotides, 2'-O-(2-methoxyethyl) (MOE) nucleotides, locked nucleic acid (LNA) nucleotides, phosphorothioate (PS) linkages, and combinations thereof. In some preferred embodiments, the modified siRNA may comprise 2'-O-Me purine and/or pyrimidine nucleotides, such as, for example, 2'-O-Me-guanosine nucleotides, 2'-O-Me-uridine nucleotides, 2'-O-Me-adenosine nucleotides, 2'-O-Me-cytosine nucleotides, and mixtures thereof. Either or both sense and/or antisense sequences or strands of siRNA or shRNA according to embodiments of present invention may comprise one or more synthesized or modified nucleotides.

In addition, siRNA compositions may further contain bioconjugates which may be useful to: (1) further increase their thermodynamic and nuclease stability; (2) improve the biodistribution and pharmacokinetic profiles of siRNAs; and/or (3) target them to specific cell types. For further discussion of available chemical modifications and bioconjugates that may be used in combination with embodiments of compositions and methods of the present invention, see, e.g., De Paula, D. et al., "Hydrophobization and bioconjugation for enhanced siRNA delivery and targeting," *RNA* 13:431-56 (2007); Chen, Y. et al., "RNAi for Treating Hepatitis B Viral Infection," *Pharmaceutical Research* 25(1):72-86 (2008); and Kim, D. et al., "RNAi mechanisms and applications," *Biotechniques* 44(5):613-16 (2008), the entire disclosures and contents of which are hereby incorporated by reference.

According to some embodiments, the sense RNA strand or sequence of the siRNA or shRNA directed against cyclophilin A is from about 19 to about 29 nucleotides long. For example, embodiments of the sense strand of the present invention may be from 20 to 28 nucleotides long, such as from 21 to 25 nucleotides long. Therefore, these sense strands of siRNA molecules may be 19, 20, 21, 22, 23, 24, 25, 26, 27, 28, or 29 nucleotides in length. Similarly, the antisense strand of embodiments of the siRNA of the present invention may also be from 19 to 29 nucleotides long, for example, from 20 to 28 nucleotides long, such as from 21 to 25 nucleotides long. Therefore, these antisense strands of siRNA molecules may be 19, 20, 21, 22, 23, 24, 25, 26, 27, 28, or 29 nucleotides in length. According to some embodiments, such lengths correspond exactly to the length of a region of complementarity between sense and antisense RNA sequences of siRNA or shRNA. Such regions of complementarity present within sense and antisense strands or sequences may have the same length. However, such sense and antisense strands may further contain non-complementary sequences, such as 3' overhangs (see below).

The at least 19 contiguous nucleotides of both sense RNA sequence and antisense RNA sequence of siRNA or shRNA may directly hybridize to one another along most if not all of such length. According to some embodiments of the present invention, the sense and antisense strands or sequences of the siRNA or shRNA composition may only contain sequences that are complementary to the other strand or sequence. However, according to other embodiments, the sense and antisense strands or sequences of the siRNA or shRNA composition may further contain other non-complementary sequences that may provide different functions for the siRNA or shRNA composition that do not contribute to base-pairing between the sense and antisense strands or sequences.

According to some embodiments, the sense and antisense strands of the siRNA may comprise two complementary, single-stranded RNA molecules. According to other embodiments, however, the sense RNA sequence and the antisense RNA sequence may be encoded by a single molecule with the two complementary sequences (corresponding to sense and antisense strands) covalently linked by a single-stranded "hairpin" or loop sequence. Without being bound by any theory, it is believed that the hairpin sequence of the latter type of the shRNA is cleaved intracellularly by the "Dicer" protein (or its equivalent) to form an siRNA or equivalent that may then be used to achieve RNAi-mediated degradation of a target (See, e.g., Tuschl, T., "Expanding small RNA interference," *Nat. Biotechnol,* 20(5):446-448 (2002)). The hairpin sequence may be from about 4 to about 12 nucleotides in length. For example, the hairpin sequence may be 9 nucleotides in length.

As an example of an embodiment of a shRNA of the present invention, SEQ ID NO: 3 provides a sequence having a sense RNA sequence and an antisense RNA sequence covalently attached by a hairpin sequence. However, such shRNA merely provides an example of a sense and antisense sequence attached by a hairpin sequence. Any acceptable hairpin sequence may be used to covalently link any sense sequence with any antisense sequence of the present invention as described herein. Indeed, embodiments of the present invention may comprise any sense sequence and antisense sequence described herein attached by any acceptable hairpin sequence, such as 5'-UUCAAGAGA-3'. However, it is to be understood that since a hairpin sequence does not necessarily correspond to a sequence within a targeted gene, such as CyPA, any acceptable hairpin sequence may be used as a part of embodiments for shRNAs of the present invention.

The embodiments of siRNA or shRNA compositions of the present invention may comprise partially purified RNA, substantially pure RNA, synthetic RNA, or recombinantly produced RNA, as well as altered RNA that differs from naturally-occurring RNA by the addition, deletion, substitution, synthesis, and/or modification of one or more nucleotides. Such modifications may include addition of non-nucleotide material, such as to the end(s) of the siRNA or to one or more internal nucleotides of the siRNA, including modifications that make the siRNA or shRNA more effective or resistant to nuclease digestion.

In addition to complementary sequences, one or both strands of embodiments of the siRNA or shRNA compositions of the present invention may further comprise a 5' overhang and/or a 3' overhang. According to some embodiments, either or both strands of the siRNA may comprise a 3' overhang of from 1 to about 6 nucleotides (which may include either ribonucleotides or deoxyribonucleotides) in length, for example, from 1 to about 5 nucleotides in length, including from 1 to about 4 nucleotides in length, such as 2 to 4 nucleotides in length. According to those embodiments in which both strands of the siRNA comprise a 3' overhang, the length of the overhangs may be the same or different for each strand. According to some embodiments, the 3' overhang present on either or both strands of the siRNA may be 2 nucleotides in length. For example, each strand of the siRNA of the invention may comprise 3' overhangs of dithymidylic acid ("TT") or diuridylic acid ("UU") or other effective dinucleotide combination known in the art. The 5' end of one or both strands or sequences of a siRNA or shRNA may also contain a phosphate group.

In order to enhance the stability of the present siRNA or shRNA, the 3' overhangs may be also stabilized against degradation. For example, the overhangs may be stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, may be tolerated and not affect the efficiency of RNAi degradation. In particular, the absence of a 2'-hydroxyl in the 2'-deoxythymidine may significantly enhance the nuclease resistance of the 3' overhang in tissue culture medium. Despite being made predominantly of ribonucleotides, it is also possible that embodiments of the siRNAs or shRNAs of the present invention may be synthesized or modified to contain one or more deoxyribonucleotides in addition to ribonucleotides along the length of one or both strands or sequences to improve efficacy or stability as the case may be.

siRNA Preparation

Embodiments of siRNA or shRNA compositions may be prepared in a number of ways, such as by chemical synthesis, in vitro transcription or digestion, or by endogenous expression. For further discussion of methods of siRNA production or synthesis, see, e.g., De Paula, D. et al., "Hydrophobization and bioconjugation for enhanced siRNA delivery and targeting" *RNA* 13:431-56 (2007); Chen, Y. et al., "RNAi for Treating Hepatitis B Viral Infection," *Pharmaceutical Research*

25(1):72-86 (2008); and Kim, D. et al., "RNAi mechanisms and applications," *Biotechniques* 44(5):613-16 (2008), the entire disclosures and contents of which are hereby incorporated by reference.

By way of example, in vitro transcription may be performed with a T7 polymerase, and siRNA digestion may be carried out by treating long double stranded RNA (dsRNA) prepared by one of the two previous methods with Dicer enzyme. Dicer enzyme may create mixed populations of dsRNA from about 21 to about 23 base pairs in length from dsRNA that is from about 500 base pairs to about 1000 base pairs in size. Dicer enzyme may effectively cleave modified strands of dsRNA, such as 2'fluoro-modified dsRNA. The Dicer enzyme method of preparing embodiments of siRNAs of the present invention may be performed using a Dicer siRNA Generation Kit available from Gene Therapy Systems (San Diego, Calif.).

In one embodiment, the siRNA may be synthetically produced. By way of example and not of limitation, embodiments of the siRNAs of the present invention may be chemically synthesized using appropriately protected ribonucleotides phosphoramidites with a conventional DNA/RNA synthesizer. The siRNA may be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo. USA), Pierce Chemical (part of Perbio Science, Rockford, Ill., USA), Glen Research (Sterling, Va. USA), ChemGenes (Ashland, Mass. USA) and Cruachem (Glasgow, UK).

The embodiments of siRNA of the present invention may also be recombinantly produced in vitro using plasmid vectors. A variety of different vectors may be employed for producing siRNAs by recombinant techniques. Such vectors are well known in the art and may include, e.g., chromosomal or nonchromosomal vectors, derivatives of SV40, bacterial plasmids, phage, baculovirus, yeast plasmids, vectors derived from combinations of plasmids and phage DNA, viral DNA such as vaccinia, adenovirus, fowl pox virus, and pseudorabies. However, any vector may be used as long as it is replicable and viable in a desired host for expression. The embodiments of siRNA of the present invention may be expressed from a recombinant plasmid either as two separate, complementary RNA molecules, or as a single RNA molecule with two complementary regions, such as a shRNA.

Plasmids suitable for expressing embodiments of siRNAs or shRNAs of the present invention, methods for inserting nucleic acid sequences expressing or encoding siRNAs or shRNAs into a plasmid, and methods for delivering recombinant plasmids to cells of interest are known in the art. See, for example, Tuschl, T., "Expanding small RNA interference," *Nat. Biotechnol.* 20(5):446-448 (2002); Brummelkamp, T. R. et al., "A system for stable expression of short interfering RNAs in mammalian cells," *Science* 296(5567): 550-553 (2002); Miyagishi M et al., "U6 promoter-driven siRNAs with four uridine 3' overhangs efficiently suppress targeted gene expression in mammalian cells," *Nat. Biotechnol.* 20(5):497-500 (2002); Paddison, P. J. et al., "Short hairpin RNAs (shRNAs) induce sequence-specific silencing in mammalian cells," *Genes Dev.* 16(8):948-58 (2002); Lee, N. S. et al., "Expression of small interfering RNAs targeted against HIV-1 rev transcripts in human cells," *Nat. Biotechnol.* 20(5):500-505 (2002); Paul, C. P. et al., "Effective expression of small interfering RNA in human cells," *Nat. Biotechnol.* 20(5): 505-508 (2002); De Paula, D. et al., "Hydrophobization and bioconjugation for enhanced siRNA delivery and targeting," *RNA* 13: 431-56 (2007); Chen, Y. et al., "RNAi for Treating Hepatitis B Viral Infection," *Pharmaceutical Research* 25(1):72-86 (2008); and Kim, D. et al., "RNAi mechanisms and applications," *Biotechniques* 44(5): 613-16 (2008), the entire disclosures and contents of which are hereby incorporated by reference.

siRNA or shRNA molecules may also be endogenously produced in cells being tested. For example, extra-chromosomal plasmids or vectors may be introduced into cells via electroporation, microinjection, or complex formation with synthetic carriers (such as lipids, polymers, or peptides). Such plasmids or vectors may be transiently or stably expressed by cells. Alternatively, siRNA or shRNA molecules may also be produced from viral vectors. Viral vectors suitable for use in the present invention are well known in the art. See, for example, Dornburg, R., "Reticuloendotheliosis viruses and derived vectors," *Gene Therap.* 2:301-310 (1995); Eglitis, M. A., "Retroviral vectors for introduction of genes into mammalian cells," *Biotechniques* 6(7):608-614 (1988); Miller A D, *Hum Gene Therap.* 1:5-14 (1990); Anderson, W. F., "Human gene therapy," *Nature* 392 (6679 Suppl.):25-30 (1998); De Paula, D. et al., "Hydrophobization and bioconjugation for enhanced siRNA delivery and targeting. RNA," 13:431-56 (2007); Chen, Y. et al., "RNAi for Treating Hepatitis B Viral Infection," *Pharmaceutical Research* 25(1):72-86 (2008); and Kim, D. et al., "RNAi mechanisms and applications" *Biotechniques* 44(5):613-16 (2008), the entire disclosures and contents of which are hereby incorporated by reference.

Appropriate DNA segments may be inserted into a vector by a variety of procedures. In general, DNA sequences may be inserted into an appropriate restriction endonuclease site(s) by procedures known in the art, which may be performed without undue experimentation by a skilled artisan. A DNA segment in an expression vector may be operatively linked to an appropriate expression control sequence(s) (i.e., a promoter) to direct siRNA or shRNA synthesis. Such promoters may include any promoter known in the art for expression either in vivo or in vitro. Suitable eukaryotic promoters may include, e.g., CMV immediate early promoter, the herpes simplex virus (HSV) thymidine kinase promoter, the early and late SV40 promoters, the promoters of retroviral long terminal repeats (LTRs), such as those of the Rous Sarcoma Virus (RSV), and metallothionein promoters, such as the mouse metallothionein-I promoter. The promoters used in embodiments of the present invention may include RNA polymerase III promoters. For example, the promoters may be selected from the group consisting of the U6, H1, 5S, 7SK, and tRNA promoters, e.g., the promoter is a U6 or a H1 promoter.

The promoters which may be used in embodiments of the present invention may also be inducible, such that expression may be turned "on" or "off." For example, a tetracycline-regulatable system employing the U6 promoter may be used to control the production of siRNA. Additionally, promoters which are tissue specific or respond to a particular stimulus may also be used. By way of example and not of limitation, tissue specific promoters include promoters which are active in the liver, such as, e.g., albumin promoter. Promoters which respond to a particular stimulus may include, e.g., heat shock protein promoters, and Tet-off and Tet-on promoters.

In addition, the expression vectors may contain one or more selectable marker genes, such as dihydrofolate reductase or neomycin resistance for eukaryotic cell culture, to allow selection of transformed host cells or cells being treated. In addition, one or more selectable markers may be used to allow selection in prokaryotic cells, such as tetracycline or ampicillin resistance.

According to some embodiments of the present invention, a vector may be provided comprising a DNA segment encoding a sense RNA strand operably linked to a first promoter and an antisense (opposite) RNA strand operably linked to a second promoter. According to this embodiment, each RNA strand or sequence may be independently expressed, and the promoter driving expression of each strand may be the same or different from the other promoter used to express the other strand or sequence. In other embodiments, the vector used to express each strand of an embodiment of siRNA of the present invention may include opposing promoters. For example, the vector may contain two promoters, such as a T7 or U6 promoter, on either side of a DNA segment encoding each strand of the siRNA and placed in opposing orientations, with or without a transcription terminator placed between the two opposing promoters. See., e.g., Wang, Z. et al., "Inhibition of *Trypanosoma brucei* Gene Expression by RNA Interference Using an Integratable Vector with Opposing T7 Promoters," *J. Biol. Chem.* 275:40174-40179 (2000), the entire disclosure and contents of which is hereby incorporated by reference.

According to other embodiments, the DNA segments encoding both siRNA strands are under the control of a single promoter. According to some other embodiments, the DNA segment encoding each complementary strand (i.e., sense and antisense strands) may contain a hairpin or loop region interspersed or inserted between the two complementary strands or sequences, such that transcription yields one RNA transcript with both complementary sequences covalently linked by a hairpin or loop (which may be referred to as "shRNA"). The single transcript may, in turn, anneal to itself creating a "hairpin" RNA structure capable of inducing RNAi. The hairpin or loop may be from about 4 to about 12 nucleotides in length, such as 9 nucleotides in length.

As an embodiment of an shRNA of the present invention, SEQ ID NO: 3 may provide a sequence having a sense RNA sequence and an antisense RNA sequence covalently attached by a hairpin sequence. However, such shRNA merely provides an example of a sense and antisense sequence attached by a hairpin sequence. Any acceptable hairpin sequence may be used to covalently link any sense sequence with any antisense sequence according to embodiments of the present invention as described herein. For example, embodiments of the present invention may comprise any sense sequence and antisense sequence described herein attached by any acceptable hairpin sequence, such as 5'-UUCAAGAGA-3'. It is to be understood that since a hairpin sequence does not necessarily correspond to a sequence within a targeted gene, such as CyPA, any acceptable hairpin sequence may be used as part of shRNA embodiments of the present invention.

Detection of siRNA Inhibition

The ability of a particular siRNA or shRNA composition to cause RNAi-mediated degradation of a target mRNA, reduce expression of a target protein, and/or inhibit virus infection and reproduction in cells may be evaluated using standard techniques. For example, any of the methods described herein may be used. In the recent years, development of cell culture systems permissible for HCV replication and infection has greatly aided in vitro study of HCV as described in, e.g., Lohmann et al., "Replication of subgenomic hepatitis C virus in a hepatoma cell line. Science," 285:110-113 (1999); Blight et al., "Efficient initiation of HCV RNA replication in cell culture," Science 290:1972-1974 (2000); Wakita, T. et al., "Production of hepatitis C virus in tissue culture from a cloned viral genome," *Nature Medicine* 11(7):791-6 (2005); Lindenbach, B. D. et al., "Complete replication of hepatitis C virus in cell culture," *Science* 309:623-626 (2005); and Zhong, J. et al., "Robust hepatitis C virus infection in vitro" *PNAS* 102(26):9294-9 (2005), the entire disclosures and contents of which are hereby incorporated by reference.

For example, Wakita et al. developed an HCV genotype 2a replicon (JFH-1) that replicates efficiently in Huh-7 cells, other human hepatocyte-derived cells (e.g., HepG2 and IMY-N9), and nonhepatic cells (e.g., HeLa and HEK293) without adaptive mutations but with lower infection efficiency. This JFH-1 genome also turned out to be capable of producing infectious viruses in cell culture. Using part of the JFH-1 genome, Lindenbach et al. (supra) described a full-length HCV genome that replicated and produced virus particles that are infectious in cell culture (HCVcc). Replication of HCVcc is robust, producing nearly $10^5$ infectious units per milliliter within 48 hours. Virus particles are filterable and neutralized with a monoclonal antibody against the viral glycoprotein E2.

As another example, Zhong et al. also developed a robust in vitro infection system based on Huh-7-derived cell lines and the JFH-1 consensus clone. This system yields viral titers of $10^4$-$10^5$ infectious units per ml of culture supernatant. In addition, infection spreads throughout the culture within a few days after inoculation at low multiplicities of infection (moi), and the virus can be serially passaged without loss in infectivity.

Thus, in order to test the efficacy of a siRNA or shRNA to prevent or treat HCV replication and/or infection, the following exemplary general protocol may be used. Briefly, HCV RNA may be delivered to cells by electroporation or liposome-mediated transfection. For purposes of electroporation, trypsinized cells that are to be transformed with HCV RNA are washed twice with and resuspended in serum-free Opti-MEM (Invitrogen) at $1\times10^7$ cells per ml. Ten micrograms of HCV RNA is mixed with 0.4 ml of the cells in a 4-mm cuvette, and a Bio-Rad Gene Pulser system is used to deliver a single pulse at 0.27 kV, 100 ohms, and 960 µF. The cells are then plated in a T162 Costar flask (Corning). Liposome mediated transfection may be performed with Lipofectamin 2000 (Invitrogen) at an RNA/lipofectamin ratio of 1:2 by using 5 µg of HCV RNA in cell suspensions containing $10^4$ cells. Cells are plated in DMEM with 20% FCS for overnight incubation. Whether HCV RNA is introduced by electroporation or liposome-mediated, transfected cells are transferred to complete DMEM and cultured for at least two days. Cells are passaged every 3-5 days. The presence of HCV in these cells and corresponding supernatants may be determined before transfection of siRNA or shRNA into the cells, and at desired time points after transfection of the cells with siRNA or shRNA. The siRNA or shRNA compositions, or DNA compositions or vectors encoding such siRNAs or shRNAs, may be introduced into HCV positive cells by any known method including those described in the present application. However, the above example is merely exemplary. One skilled in the art may readily perform modifications to the above protocol or use entirely different methods known in the art.

Total cellular RNA may be isolated by the guanidine thiocyanate method by using standard protocols, and RT-QPCR analysis may be performed as described in, e.g., Kapadia, S. B. et al., "Hepatitis C virus RNA replication is regulated by host geranylgeranylation and fatty acids" *PNAS* 102:2561-2566 (2005). For RT-QPCR, HCV and GAPDH transcript levels may be determined relative to a standard curve comprised of serial dilutions of plasmid containing the HCV cDNA or human GAPDH gene. According to one example for titration of HCV, cell supernatants may be, e.g., serially diluted 10-fold in complete DMEM and used to infect $10^4$ naive Huh-7.5.1 or Huh-7 cells per well in 96-well plates (Corning). According to this example, the inoculum is incubated with cells for 1 h at 37° C. and then supplemented with fresh complete DMEM. The level of HCV infection may then be determined, e.g., 3 days post-infection by immunofluorescence staining for HCV NS5A. The viral titer is expressed as focus-forming units per milliliter of supernatant (ffu/ml), determined by the average number of NS5A-positive foci detected at the highest dilutions. HCV RNA levels and the number of NS5A-positive foci obtained before and after the introduction of siRNA into cells may be used to determine the efficacy of siRNA in treating HCV. Additional methods that are well known in the art for determining the levels of HCV in cells before and after the siRNA treatment may also be used.

RNAi-mediated degradation of target mRNA by a siRNA or shRNA containing a given target sequence may also be evaluated using animal models for HCV infection. In one embodiment, chimpanzees are used. By way of example, HCV RNA has been delivered to chimpanzees by at least one intrahepatic injection. See, e.g., Kolykhalov et al., "Transmission of hepatitis C by intrahepatic inoculation with transcribed RNA," *Science* 277:570-574 (1997). According to this example, serum samples are collected, e.g., every 2 weeks to test for HCV replication. Briefly, tests that may be done include assays for liver enzymes, antibodies to HCV and viremia, as determined by quantifying circulating HCV RNA by branched DNA and quantitative-competitive (QC) RT-PCR. After a desirable time period, e.g., two months, HCV positive chimpanzees may be administered embodiments of a siRNA or shRNA of the present invention, such as by infection with lentiviral vectors encoding such siRNA or shRNA. The siRNA or shRNA compositions may be delivered once or as many times as necessary to control the infection. Serum samples are again collected at predetermined time periods, e.g., every two weeks to determine the levels of HCV replication by the same tests as described above. The efficacy of a particular siRNA or shRNA may be established by comparing the results of the tests performed before and after siRNA administration. For example, stabilization of levels of liver enzymes and/or lower numbers of circulating HCV may be used to indicate that siRNA is effective at reducing HCV replication and/or infection.

Another animal model that may be used is a chimeric scid/Alb-uPA mouse, which expresses urokinase-type plasminogen activator under the control of the albumin promoter. Since the expression of this transgene is toxic to mouse hepatocytes, these mice either die early due to a bleeding phenotype or at 2-3 weeks of age due to liver failure. See, e.g., Heckel et al., "Neonatal bleeding in transgenic mice expressing urokinase-type plasminogen activator," *Cell* 62:447-456 (1990). However, these mice may be transplanted with human hepatocytes, resulting in repopulation of mouse liver. Once these mice are transplanted to achieve chimeric liver, they may be used as a model for HCV infection. Briefly, once infected with HCV, these mice may be treated with a siRNA or shRNA of the present invention to determine its efficacy against HCV. The same types of assays as described above for the chimpanzee model may be used. Furthermore, mice may be sacrificed and their livers examined histologically for HCV infection and/or tissue damage.

As another example, cells from an individual, subject, or patient infected with HCV may be treated with embodiments of a siRNA or shRNA composition of the present invention in vitro and tested for RNAi-mediated degradation of target mRNA. Methods for isolating and culturing cells from a patient are well known in the art.

siRNA Delivery

In embodiments of the methods of the present invention, the siRNA of shRNA may be administered to an individual, subject, or patient either as a naked siRNAs and/or shRNAs or as part of a recombinant plasmid or vector expressing such siRNAs and/or shRNAs, which may also be delivered in conjunction with a delivery reagent. Alternatively, embodiments of the siRNA or shRNA compositions of the present invention may be administered as a viral vector(s) encoding either separate sense and antisense siRNA strands or a single shRNA. When naked siRNAs, shRNAs, or recombinant plasmids or vectors expressing a siRNA or shRNA are administered directly to cells, such delivery may be achieved, for example, by electroporation, gene gun, microinjection, or complex formation with synthetic carriers (such as lipids, polymers, and/or peptides). In addition, embodiments of the siRNAs or shRNAs of the present invention may be delivered as a pharmaceutical composition in combination with a pharmaceutically acceptable carrier.

Suitable delivery reagents for administration in conjunction with the siRNA or shRNA may include cationic polymers and lipids as well as encapsulated lipid particles, such as liposomes, etc. Examples may include Mirus Transit TKO lipophilic reagent, lipofectin, lipofectamine, cellfectin, or polycations (e.g., polylysine), or liposomes. For further discussion of effective delivery reagents that may be used in combination with present siRNA compositions, see, e.g., De Paula, D. et al. "Hydrophobization and bioconjugation for enhanced siRNA delivery and targeting," *RNA* 13:431-56 (2007); Chen, Y. et al., "RNAi for Treating Hepatitis B Viral Infection," *Pharmaceutical Research* 25(1):72-86 (2008); and Kim, D. et al., "RNAi mechanisms and applications," *Biotechniques* 44(5):613-16 (2008), the entire disclosures and contents of which are hereby incorporated by reference. See also, e.g., U.S. patent application Ser. Nos. 11/598,052, 11/978,398, 11/978,455, 11/978,457, 11/746,864, 11/750,553, and 10/597,431, the entire disclosures and contents of which are hereby incorporated by reference.

According to some embodiments, the delivery reagent may be a liposome. Liposomes may be used to aid in the delivery of the siRNA or shRNA to a particular tissue, such as the liver, and can also increase the blood half-life of the siRNA. The selection of lipids is generally guided by consideration of factors such as the desired liposome size and half-life of the liposomes in the blood stream. Methods for the preparation of liposomes as delivery agents that may be used in combination with embodiments of compositions and methods of the present invention are well known in the art. For example, see Szoka et al., "Comparative properties and methods of preparation of lipid vesicles (liposomes)," *Ann. Rev. Biophys. Bioeng.* 9:467 (1980); Immordino, M. L., "Stealth liposomes: review of the basic science, rationale, and clinical applications, existing and potential," *Int. J. Nanomedicine* 1(3):297-315 (2006); Samad, A, "Liposomal Drug Delivery Systems: An Update Review," *Current Drug Delivery* 4(4):297-305 (2007); and U.S. Pat. Nos. 4,235,871, 4,501,728, 4,837,028, and 5,019,369, the entire disclosures and contents of which are hereby incorporated by reference. The liposomes encapsulating the siRNA may comprise a ligand molecule that targets the liposome to the liver. Such ligands may include, but are not limited to, ligand of the asialoglycoprotein receptor (ASGPR), β-sitosterol-β-d-glucoside (sito-G), galactosylated liposomes, asialofetuin grafted vesicles, liposomes that are modified with human serum albumin, and mannosylated liposomes. See, e.g., Chen, Y. et al., "RNAi for Treating Hepatitis B Viral Infection," *Pharmaceutical Research* 25(1): 72-86 (2008); and Pathak, A., "Nanovectors for efficient liver specific gene transfer," *Int. J. Nanomedicine* 3(1):31-49 (2008), the entire disclosures and contents of which are hereby incorporated by reference.

The liposomes encapsulating the siRNA may also be modified so as to avoid clearance by the mononuclear macrophage and reticuloendothelial systems, for example by having opsonization-inhibition moieties bound to the surface of the structure. In one embodiment an embodiment of a liposome of the present invention may comprise both opsonization-inhibition moieties and a ligand. Opsonization-inhibiting moieties for use in preparing the embodiment of the liposomes of the present invention may be large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016. Liposomes modified with opsonization-inhibition moieties thus remain in the circulation much longer than unmodified liposomes and are sometimes called "stealth" liposomes.

Opsonization-inhibiting moieties suitable for modifying liposomes are generally water-soluble polymers with a number-average molecular weight from about 500 to about 40,000 daltons, and more preferably from about 2,000 to about 20,000 daltons. Such polymers may include polyethylene glycol (PEG) or polypropylene glycol (PPG) derivatives; e.g., methoxy PEG or PPG, and PEG or PPG stearate synthetic polymers such as polyacrylamide or poly N-vinyl pyrrolidone; linear, branched, or dendrimeric polyamidoamines; polyacrylic acids; polyalcohols, e.g., polyvinylalchohol and polyxylitol to which carboxylic or amino groups are chemically linked, as well as gangliosides, such as ganglioside $GM_1$. Copolymers of PEG, methoxy PEG, or methoxy PPG, or derivatives thereof, may also be suitable. In addition, the opsonization inhibiting polymer may be a block copolymer of PEG and either a polyamino acid, polysaccharide, polyamidoamine, polyethyleneamine, or polynucleotide. The opsonization-inhibiting polymers may also be natural polysaccharides containing amino acids or carboxylic acids, e.g., galacturonic acid, glucuronic acid, mannuronic acid, hyaluronic acid, pectic acid, neuraminic acid, alginic, acid, carrageenan; aminated polysaccharides or oligosaccharides (linear or branched); or carboxylated polysaccharides or oligosaccharides, e.g., reacted with derivatives of carbonic acids with resultant linking of carboxylic groups. For example, the opsonization-inhibiting moiety may be a PEG, PPG, or derivatives thereof. Liposomes modified with PEG or PEG-derivatives are sometimes called "PEGylated liposomes."

The opsonization-inhibiting moiety may be bound to the liposome membrane by any one of numerous well-known techniques. For example, an N-hydroxysuccinimide ester of PEG may be bound to a phosphatidyl-ethanolamine lipid-soluble anchor and then bound to a membrane. Similarly, a dextran polymer may be derivatized with a stearylamine lipid-soluble anchor via reductive amination using Na(CN)BH3 and a solvent mixture such as tetrahydrofuran and water in a 30:12 ratio at 60° C.

The vector containing the appropriate DNA sequence as described herein, as well as an appropriate promoter or control sequence, may be employed to transform an appropriate host to permit the host to express the siRNA or shRNA. Appropriate cloning and expression vectors for use with prokaryotic and eukaryotic hosts have been described and are well known in the art. See, e.g., Sambrook, et al., Molecular Cloning: A Laboratory Manual, (Second Edition, Cold Spring Harbor, N.Y. 1989). In one embodiment, the cells used to produce the siRNAs or shRNAs may be HEK 293T cells.

As described above, embodiments of the siRNA or shRNA compositions of the present invention may also be delivered using viral vectors by modifying methods generally known in the art. Examples of viral vectors that may be suitable for use with embodiments of methods of the present invention may include retroviral, adenoviral, and adeno-associated viral vectors. Any viral vector capable of encoding or accepting coding sequences for a siRNA or shRNA molecule(s) to be expressed may be used including, for example, vectors derived from adenovirus (AV), adeno-associated virus (AAV), retroviruses (e.g., lentiviruses), Rhabdoviruses, herpes virus, etc. According to some preferred embodiments, viral vectors that may be used to deliver embodiments of siRNA compositions of the present invention may include lentiviruses or lentiviral-derived vectors. The tropism of the viral vectors may also be modified by pseudotyping the vectors with envelope proteins or other surface antigens from other viruses. For example, an AAV vector of the invention may be pseudotyped with surface proteins from vesicular stomatitis virus (VSV), rabies, Ebola, Marburg, and the like. According to some embodiments, siRNAs or shRNA may be expressed using RNA polymerase III promoters, such as U6, H1, or tRNA promoters.

For further review and discussion of viral vectors that may potentially be used in combination with the present invention, see, e.g., De Paula, D. et al., "Hydrophobization and bioconjugation for enhanced siRNA delivery and targeting," *RNA* 13:431-56 (2007); Chen, Y. et al., "RNAi for Treating Hepatitis B Viral Infection," *Pharmaceutical Research* 25(1):72-86 (2008); and Kim, D. et al., "RNAi mechanisms and applications," *Biotechniques* 44(5):613-16 (2008), the entire disclosures and contents of which are hereby incorporated by reference.

Suitable enteral administration routes for administering embodiments of siRNA or shRNA compositions of the present invention include oral, rectal or intranasal delivery. Suitable parenteral administration routes may include intravascular administration (e.g., intravenous bolus injection, intravenous infusion, intra-arterial bolus injection, intra-arterial infusion and catheter instillation into the vasculature); peri- and intra-tissue administration (e.g., intra-hepatic injection), subcutaneous injection or deposition including subcutaneous infusion (such as by osmotic pumps), direct application to the area at or near a site of infection or risk of infection (e.g., by a catheter or other placement device), and inhalation. In an embodiment, injections or infusions of the siRNA or shRNA are given directly into the liver or adjacent thereto. See, e.g., Chen, Y. et al., "RNAi for Treating Hepatitis B Viral Infection," Pharmaceutical Research 25(1):72-86 (2008), the entire disclosure and contents of which is hereby incorporated by reference.

The above-mentioned general methods for siRNA or shRNA delivery to cells may be further exemplified without limitation by the following specific examples of gene therapy techniques for mammalian liver. For example, cultured hepatocytes have been genetically modified by retroviral vectors (Wolff, J. A. et al., *PNAS* 84:3344-3348 (1987); Ledley, F. D. et al., *PNAS* 84:5335-5339 (1987)) and re-implanted back into the livers in animals and in people (J. R. Chowdhury et al., *Science* 254:1802 (1991); Grossman, M. et al., *Nature Genetics* 6:335 (1994)). Retroviral vectors have also been delivered directly to livers in which hepatocyte division is induced by partial hepatectomy (Kay, M. A. et al., *Hum Gene Ther.* 3:641-647 (1992); Ferry, N. et al., *PNAS* 88:8377-8381 (1991); Kaleko, M. et al., *Hum Gene Ther.* 2:27-32 (1991). The injection of adenoviral vectors into the portal or systemic circulatory systems led to high levels of foreign gene expression that is transient (Stratford-Perricaudet, L. D. et al., *Hum. Gene Ther.* 1:241 (1990); Jaffe, H. A. et al., *Nat. Genet.* 1:372 (1992); Li, Q. et al., *Hum. Gene Ther.* 4:403 (1993). Non-viral transfer methods may include polylysine complexes of asialoglycoproteins that are injected into the system circulation (Wu, G. Y. et al., *Biol. Chem.* 263:14621-14624 (1988)). Foreign gene expression has also been achieved by repetitively injecting naked DNA in isotonic solutions into the liver parenchyma of animals treated with dexamethasone (Malone, R. W. et al., *JBC* 269:29903-29907 (1994); Hickman, M. A., *Human Gene Ther.* 5:1477-1483 (1994). Plasmid DNA expression in the liver has also been achieved via liposomes delivered by tail vein or intraportal routes (Kaneda, Y. et al., *Biol. Chem.* 264:12126-12129 (1989); Soriano, P. et al., *PNAS* 80:7128-7131 (1983); Kaneda, Y., et al., *Science* 243: 375-378 (1989). However, it is to be understood that any appropriate siRNA or shRNA delivery method that is currently known or available in the art may be used in combination with or as part of embodiments of compositions and methods of the present invention. For example, transposon-mediated vectors may be used to deliver siRNA or shRNA compositions of the present invention to cells.

Embodiments of compositions of the present invention used in combination with delivery reagents may comprise an siRNA comprising a sense RNA sequence and an antisense RNA sequence, wherein sense RNA sequence of siRNA may be at least about 70% homologous to at least 19 contiguous nucleotides between nucleotide 155 and nucleotide 183 of the coding sequence of human cyclophilin A cDNA (accession number Y00052; SEQ ID NO: 1) with antisense RNA sequence complementary to such sense RNA sequence (i.e., able to hybridize to the sense RNA sequence at a physiological temperature). However, the degree of homology between sense strand of siRNA and the at least 19 contiguous nucleotides of CyPA between nucleotides 155 and 183 of the coding sequence of CyPA cDNA may be higher, such as, for example, at least about 80%, 90%, 95%, or 100% homologous or identical, with antisense strand complementary thereto. According to one embodiment, sense strand of siRNA composition may comprise SEQ ID NO: 2 corresponding to nucleotides 159 through 179 of CyPA cDNA along with an antisense strand complementary thereto.

Described a different way, such delivery embodiments of compositions of the present invention may comprise a siRNA comprising a sense RNA sequence and an antisense RNA sequence, wherein the antisense RNA sequence of the embodiment of siRNA of the present invention may be at least about 70% complementary to at least 19 contiguous nucleotides between nucleotide 155 and nucleotide 183 of the coding sequence of human cyclophilin A cDNA (accession number Y00052; SEQ ID NO: 1) with sense RNA sequence complementary to such antisense RNA sequence (i.e., able to hybridize to the sense RNA sequence at a physiological temperature). However, the degree of complementarity between antisense strand of siRNA and the at least 19 contiguous nucleotides of CyPA between nucleotides 155 and 183 of the coding sequence of CyPA cDNA may be higher, such as, for example, at least about 80%, 90%, 95%, or 100% complementary, with a sense RNA sequence complementary thereto. As an example, antisense sequence may comprise SEQ ID NO: 4.

As described above, such sense and antisense RNA sequences of embodiments of the present invention may be alternatively expressed as a single molecule covalently attached by a hairpin sequence to form a shRNA. In addition, embodiments of the present invention may include DNA polynucleotides encoding or expressing such siRNA or shRNA molecules, and such DNA polynucleotides may be constructed as part of an expression vector or plasmid. Therefore, delivery embodiments of compositions of the present invention may further include DNA polynucleotides, vectors, plasmids, and shRNAs in combination with a suitable delivery reagent. Such delivery reagents may contain two or more such siRNA, shRNA, DNA polynucleotide, vector, and/or plasmid compositions together or with other known drugs or therapies.

Pharmaceutical Compositions

The embodiments of siRNA, shRNA, or DNA compositions of the present invention may be formulated as a pharmaceutical composition in combination with a pharmaceutically acceptable carrier according to techniques known in the art. Embodiments of pharmaceutical compositions of the present invention may be characterized as being sterile and pyrogen-free. Methods for preparing embodiments of pharmaceutical compositions of the present invention are well within the skill in the art, for example as described in Remington's Pharmaceutical Science, (17th ed., Mack Publishing Company, Easton, Pa., 1985); Goodman & Gillman's: The Pharmacological Basis of Therapeutics (11th Edition, McGraw-Hill Professional, 2005); and Griffin P. et al. The Textbook of Pharmaceutical Medicine (Blackwell Publishing, Malden, Mass., 2006), the entire disclosures and contents of which are hereby incorporated by reference.

The present pharmaceutical formulations may comprise a siRNA or shRNA (e.g., 0.1 to 90% by weight), or a physiologically acceptable salt thereof, mixed with a pharmaceutically acceptable carrier. Physiologically acceptable carriers may include water, buffered water, saline solutions (e.g., normal saline or balanced saline solutions such as Hank's or Earle's balanced salt solutions), 0.4% saline, 0.3% glycine, hyaluronic acid, etc.

Such embodiments of pharmaceutical compositions of the present invention may comprise an siRNA comprising a sense RNA sequence and an antisense RNA sequence, wherein sense RNA sequence of siRNA may be at least about 70% homologous to at least 19 contiguous nucleotides between nucleotide 155 and nucleotide 183 of the coding sequence of human cyclophilin A cDNA (accession number Y00052; SEQ ID NO: 1) with antisense RNA sequence complementary to such sense RNA sequence. However, the degree of homology between sense strand of siRNA and the at least 19 contiguous nucleotides of CyPA between nucleotides 155 and 183 of the coding sequence of CyPA cDNA may be higher, such as, for example, at least about 80%, 90%, 95%, or 100% homologous or identical, with antisense strand complementary thereto. According to one embodiment, the sense strand of siRNA composition may comprise SEQ ID NO: 2 corresponding to nucleotides 159 through 179 of CyPA cDNA along with an antisense strand complementary thereto.

Described a different way, such pharmaceutical compositions may comprise an siRNA comprising a sense RNA sequence and an antisense RNA sequence, wherein antisense RNA sequence of siRNA of the present invention may be at least about 70% complementary to at least 19 contiguous nucleotides between nucleotide 155 and nucleotide 183 of the coding sequence of human cyclophilin A cDNA (accession number Y00052; SEQ ID NO: 1) with sense RNA sequence complementary to such antisense RNA sequence. However, the degree of complementarity between antisense strand of siRNA and at least 19 contiguous nucleotides of CyPA between nucleotides 155 and 183 of the coding sequence of CyPA cDNA may be higher, such as, for example, at least about 80%, 90%, 95%, or 100% complementary, with a sense RNA sequence complementary thereto. As an example, the antisense sequence may comprise SEQ ID NO: 4.

Again, as described above, such sense and antisense RNA sequences of embodiments of the present invention may be alternatively expressed as a single molecule covalently attached by a hairpin sequence to form a shRNA. In addition, embodiments of the present invention include DNA polynucleotides encoding or expressing such siRNA or shRNA molecules, and such DNA polynucleotides may be constructed as part of an expression vector or plasmid. Therefore, embodiments of pharmaceutical compositions of the present invention may further include DNA polynucleotides, vectors, plasmids, and/or shRNAs in combination with an acceptable carrier. In addition, pharmaceutical compositions may further comprise two or more different embodiments of siRNA, shRNA, DNA polynucleotide, vector, and/or plasmid compositions of the present invention, together or in combination with other known drugs or therapies.

Embodiments of pharmaceutical compositions of the present invention may be administered orally, nasally, parenterally, intrasystemically, intraperitoneally, topically (as by drops or transdermal patch), bucally, intrahepatically, or as an oral or nasal spray.

An embodiment of a pharmaceutical composition of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, etc.), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

Injectable depot forms may be made by forming microencapsule matrices of the siRNA, shRNA, etc., in biodegradable polymers such as polylactide-polyglycolide. Depending upon the ratio of drug to polymer and the nature of the particular polymer employed, the rate of release may be controlled. Examples of other biodegradable polymers may include poly(orthoesters) and poly(anhydrides). Depot injectable formulations may also prepared by entrapping the siRNA, shRNA, etc., composition in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

In some cases, to prolong the effect of siRNAs, shRNAs, etc., it is desirable to slow the absorption from subcutaneous or intramuscular injection. This may be accomplished by the use of a liquid suspension of crystalline or amorphous material with poor water solubility. The rate of absorption of the composition may then depend upon its rate of dissolution which, in turn, may depend upon crystal size and crystalline form. Alternatively, delayed absorption of a parenterally administered form may be accomplished by dissolving or suspending the drug in an oil vehicle. Prolonged absorption of the injectable pharmaceutical composition may be brought about by the inclusion of agents which delay absorption such as aluminum monostearate and gelatin.

Solid dosage forms for oral administration may include, but are not limited to, capsules, tablets, pills, powders, and granules. In such solid dosage forms, the composition of the present invention may be mixed with at least one pharmaceutically acceptable excipient or carrier, such as sodium citrate or dicalcium phosphate and/or: (a) fillers or extenders such as starches, lactose, sucrose, glucose, mannitol, and silicic acid; (b) binders such as, for example, carboxymethylcellulose, alginates, gelatin, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents such as, for example, acetyl alcohol and glycerol monostearate; (h) absorbents such as kaolin and bentonite clay; and/or (i) lubricants such as talc, calcium stearate, magnesium stearate, solid polyethylene glycols, sodium lauryl sulfate, and mixtures thereof. In the case of capsules, tablets and pills, the dosage form can also comprise buffering agents. Soft and hard filled gelatin capsules may also be used excipients, such as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and may also be of a composition that they release the active ingredient(s) only, or preferentially, in a certain part of the intestinal tract, optionally, in a delayed manner. Examples of embedding compositions which may be used may include polymeric substances and waxes.

The embodiments of the pharmaceutical compositions of the present invention may also be in micro-encapsulated form, if appropriate, with one or more of the above-mentioned excipients.

Liquid dosage forms for oral administration may include, but are not limited to, pharmaceutically acceptable emulsions, solutions, suspensions, syrups and elixirs. Liquid dosage forms may contain inert diluents commonly used in the art such as, for example, water or other solvents, solubilizing agents and/or emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions may also include adjuvants such as wetting agents, emulsifying and suspending agents, sweetening, flavoring, or perfuming agents. Suspensions may contain suspending agents, such as ethoxylated isostearyl alcohols, polyoxyethylene sorbitol and sorbitan esters, microcrystalline cellulose, aluminum metahydroxide, bentonite, agar-agar, and/or tragacanth, and mixtures thereof.

Alternatively, the composition may be pressurized and contain a compressed gas, such as nitrogen or a liquefied gas propellant. The liquefied propellant medium and indeed the total composition may preferably be such that the composition does not dissolve therein to any substantial extent. The pressurized composition may also contain a surface active agent. The surface active agent may be a liquid or solid nonionic surface active agent or may be a solid anionic surface active agent. It would be generally preferred that the solid anionic surface active agent be in the form of a sodium salt.

Embodiments of the pharmaceutical compositions of the present invention may also comprise conventional pharmaceutical excipients and/or additives. Suitable pharmaceutical excipients may include stabilizers, antioxidants, osmolality adjusting agents, buffers, and/or pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), and/or, optional additions of calcium or sodium salts (for example, calcium chloride, calcium ascorbate, calcium gluconate or calcium lactate).

Pharmaceutical compositions comprising an embodiment of a siRNA or shRNA of the present invention may include penetration enhancers to enhance their delivery, such as through the alimentary route. Penetration enhancers may be classified as belonging to one of five broad categories, i.e., fatty acids, bile salts, chelating agents, surfactants and non-surfactants (Lee et al., *Critical Reviews in Therapeutic Drug Carrier System,* 8:91-192 (1991); Muranishi, *Critical Reviews in Therapeutic Drug Carrier Systems,* 7:1-33 (1990)). One or more penetration enhancers from one or more of these broad categories may be included. Various fatty acids and their derivatives which act as penetration enhancers may include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). See, e.g., Lee et al., *Critical Reviews in Therapeutic Drug Carrier Systems*, page 92 (1991); Muranishi, *Critical Reviews in Therapeutic Drug Carrier Systems,* 7:1 (1990); El-Hariri et al., The mitigating effects of phosphatidylcholines on bile salt- and lysophosphatidylcholine-induced membrane damage," *J. Pharm. Pharmacol.* 44:651-654 (1992)).

Chelating agents may include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, page 92 (1991); Muranishi, *Critical Reviews in Therapeutic Drug Carrier Systems,* 7:1 (1990); Buur et al., *J. Control Rel.,* 14:43-51 (1990)). Chelating agents may have the added advantage of also serving as DNase inhibitors.

Surfactants may include, for example, sodium lauryl sulfate, polyoxyethylene-9-lauryl ether and polyoxyethylene-20-cetyl ether (Lee et al., *Critical Reviews in Therapeutic Drug Carrier Systems*, page 92 (1991)); and perfluorochemical emulsions, such as FC43 (Takahashi et al., *J. Pharm. Phamacol.,* 40:252-257 1988)).

Non-surfactants may include, for example, unsaturated cyclic ureas, 1-alkyl- and 1-alkenylazacyclo-alkanone derivatives (Lee et al., *Critical Reviews in Therapeutic Drug Carrier Systems,* page 92 (1991)); and non-steroidal anti-inflammatory agents such as diclofenac sodium, indomethacin and phenylbutazone (Yamashita et al., *J. Pharm. Pharmacol.,* 39:621-626 1987)).

Prevention of degradation of siRNAs, shRNAs, etc., by microorganisms may be ensured by the inclusion of various antibacterial and antifungal agents including, for example, paraben, chlorobutanol, phenol, sorbic acid, etc.

One skilled in the art will appreciate that an effective amount of siRNA, shRNA, etc. of the present invention may be determined empirically and may be employed in pure form or, where such forms exist, in a pharmaceutically acceptable salt, ester or prodrug form. A "therapeutically effective" amount of an embodiment of a siRNA, shRNA, or siRNA/shRNA-expressing vector composition of the present invention may be determined by the amount needed to treat, manage, inhibit, prevent or ameliorate adverse conditions or symptoms of HCV infection or disease. Such determination may be made according to any method known in the art or described herein, such as, e.g., by measuring the level, amount, and/or activity of HCV particles and various liver enzymes or by monitoring symptoms of infection or disease. Embodiments of compositions of the present invention may be administered to an individual, subject or patient, in need of treatment for HCV infection or at risk of HCV infection, either directly to a cell or tissue, as a pharmaceutical composition, or in combination with a delivery reagent as described above. It will be understood that, when administering compositions of the present invention to a human patient, a "therapeutically effective" amount is expressed as total daily usage of the embodiment of the composition of the present invention and may be decided by the attending physician within the scope of sound medical judgment. The specific "therapeutically effective" dose level for a particular individual, subject, or patient may depend upon a variety of factors, including, for example, the type and degree of the cellular or physiological response desired, activity of the specific siRNA or shRNA composition employed or expressed, the specific pharmaceutical formation or delivery method employed, the age, body weight, general health, sex and diet of the patient, the time of administration, route of administration, and rate of excretion of the composition in relation to HCV infection, the specific dosage regimen, drugs used in combination or coincidental with the present composition, and other factors well known in the medical arts. For example, doses of embodiments of compositions of the present compositions may be started at levels lower than those expected to be necessary to achieve the desired therapeutic effect and to gradually increase the dosages until the desired effect is achieved.

One skilled in the art may also readily determine an appropriate dosage regimen for administering the embodiments of the compositions of the present invention to a given individual, subject, or patient. For example, a siRNA, shRNA or vector composition may be administered to a subject once, such as by a single injection or deposition. Alternatively, a siRNA, shRNA or vector composition may be administered to a subject multiple times daily or weekly. For example, compositions may be administered to a subject once weekly for a period of from about three to about twenty-eight weeks, such as from about seven to about ten weeks. In an example of a dosage regimen, compositions may be injected at or near the liver once a week for seven weeks.

In another embodiment, embodiments of compositions of the present invention may be administered in combination with other agents known or used to treat hepatitis C infection. By way of example, a siRNA may be administered in combination with interferon alpha. Additional HCV treatments that may be used in combination with compositions of the present invention may include ribavirin and liver transplantation. It is also contemplated that embodiments of the siRNAs, shRNAs, etc., of the present invention may be used in combination with other siRNAs or shRNAs developed against CyPA or HCV targets and/or in combination with protease inhibitors or polymerase inhibitors developed against HCV.

In addition, embodiments of siRNA and/or shRNA compositions of the present invention may be used in combination with Cyclosporin A (CsA) to manage, treat, and/or prevent HCV infection. Embodiments of RNAi compositions of the present invention directed against CyPA may be particularly advantageous because such compositions circumvent CsA resistance of some HCV strains to effectively inhibit such CsA-resistant HCV strains when administered in combination with CsA. In other words, treatment of cells infected or at risk of infection by a CsA-resistant strain of HCV with embodiments of siRNA and/or shRNA compositions of the present invention may have the effect of "resensitizing" previously CsA-resistant HCV to CsA treatment. Thus, according to some embodiments, these compositions may provide a novel avenue for therapy against HCV when used in combination with an existing compound (CsA).

Methods

According to another embodiment of the present invention, methods are provided for administering siRNA, shRNA, viral or non-viral vector, or DNA polynucleotide compositions of the present invention directed against CyPA (as described herein) to effectively inhibit HCV infection in a cell or tissue. According to some embodiments, such methods may be used to prevent HCV infection in a cell or tissue at risk of HCV infection, such as a liver cell or tissue. According to other embodiments, such methods may be used to treat or manage HCV infection in a cell or tissue infected with HCV. Such methods may comprise administering such compositions in the form of a pharmaceutical composition in combination with acceptable carriers, etc., or alternatively, such compositions may be administered in combination with a delivery reagent as described herein. In addition, such methods may comprise administering such compositions directly to cells or tissues infected or at risk of infection by HCV without a delivery reagent as described herein.

Embodiments of methods of the present invention may be further provided for administering siRNA, shRNA, viral or non-viral vector, or DNA polynucleotide embodiments of compositions of the present invention directed against CyPA (as described herein) to effectively inhibit HCV infection in an individual, subject, or patient. According to some embodiments, such methods may be used to prevent HCV infection in an individual, subject, or patient at risk of HCV infection, such as an individual, subject, or patient exposed to HCV. According to other embodiments, such methods may be used to treat or manage HCV infection in an individual, subject, or patient infected with HCV. Again, such methods may comprise administering such compositions in the form of a pharmaceutical composition in combination with acceptable carriers, etc., or alternatively, such compositions may be administered in combination with a delivery reagent as described herein. In addition, such methods may comprise administering such compositions directly to cells or tissues infected or at risk of infection by HCV without a delivery reagent as described herein.

General Methods

Molecular biological techniques, biochemical techniques, and microorganism techniques as used herein are well known in the art and may include, for example, Innis, M. A. et al., "PCR Strategies," Academic Press (1995); Ausubel, F. M., "Short Protocols in Molecular Biology: A Compendium of Methods from Current Protocols in Molecular Biology," (Wiley & Sons, 5$^{th}$ Ed., 2002); Sninsky, J. J. et al., "PCR Applications: Protocols for Functional Genomics," (Academic Press, 1999); Sambrook J. et al., "Molecular Cloning: A Laboratory Manual," (3$^{rd}$ Ed., Cold Spring Harbor Laboratory Press, Cold Spring Harbor, N.Y., 2001); Freshney, R. I., "Culture of Animal Cells: A Manual of Basic Techniques," (4$^{th}$ Ed., 2000); Spector, D. L., Cells: "A Laboratory Manual, Culture and Biochemical Analysis of Cells," (Cold Spring Harbor Press, 1998); and the like. All relevant portions of each of these references are hereby incorporated by reference. Gene introduction may be confirmed by any standard method known in the art, such as those described herein, including, e.g., Northern blotting analysis and Western blotting analysis, or other well-known, common techniques. Any technique may be used herein for introduction of a nucleic acid molecule into cells, including, for example, transformation, transduction, transfection, and the like. Such nucleic acid molecule introduction techniques are well known in the art and commonly used.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, all examples in the present disclosure, while illustrating embodiments of the present invention, are provided as non-limiting examples and are, therefore, not to be taken as limiting the various aspects of the present invention so illustrated. Those of skill in the art should, in light of the present disclosure, appreciate that many changes can be made in the specific embodiments that are disclosed and still obtain a like or similar result without departing from the spirit and scope of the invention.

Example 1

Materials and Methods

Cells, Compounds, and Antibodies.

GS5 and RS2 cells have been described previously (36). Huh-7.5 cells and the H77 replicon construct are provided by Charles Rice and Apath LLC. CsA is purchased from Alexis Corporation (San Diego, Calif.). The following antibodies are used: anti-CyPA (Biomol, Plymouth Meeting, Pa.), anti-CyPB (Affinity BioReagents, Golden, Colo.), anti-Ku80 and antiactin (Sigma-Aldrich), anti-NS5A and anti-NS5B (Virogen, Boston, Mass.), anti-NS3 (G. George Luo, University of Kentucky), and anticore (Affinity BioReagents, Golden, Colo.).

RNA Interference.

A human immunodeficiency virus (HIV)-based lentiviral vector is used to express all of the short hairpin RNAs (shRNAs). The sh-Luc and sh-B710 RNAs have been described previously (Robida et al., "Characterization of hepatitis C virus subgenomic replicon resistance to cyclosporine in vitro," J. Virol. 81:5829-5840.). Target or sense sequences for the other shRNAs are as follows:

A-159, 5'-AAG GGT TCC TGC TTT CAC AGA-3' (SEQ ID NO: 6), which correspond to nucleotides 159-179 of human CyPA cDNA (accession no. Y00052; RNA sequence for A-159 is provided in SEQ ID NO: 2);

A-285, 5'-AAG CAT ACG GGT CCT GGC ATC-3', (SEQ ID NO: 7), which correspond to nucleotides 285-305 of human CyPA cDNA;

A-285', 5'-AAG CAT ACa GGT CCT GGC ATC-3' (SEQ ID NO: 8), which correspond to nucleotides 285-305 of human CyPA cDNA, with one mismatch represented in lower case;

A-459, 5'-AAT GGC AAG ACC AGC AAG AAG-3' (SEQ ID NO: 9), which correspond to nucleotides 459-479 of human CyPA cDNA;

C-454: 5'-AAG ACT GAA GGT GTG CTG GTA-3' (SEQ ID NO: 10), which correspond to nucleotides 454-474 of human CyPC cDNA (accession no. S71018); and NTC, 5'-AAG GAG GTG ACA TCA CCA CTG-3' (SEQ ID NO: 11), wherein NTC (no target control) does not have a target in the human genome.

The above sequences may be converted to RNA sequences by changing each thymine (T) to uracil (U). Lentiviral vector production and transduction are performed as described previously (44). Stable cells expressing shRNAs are obtained by selection with 1 µg/ml of puromycin (MP Biomedicals, Solon, Ohio) for 3 weeks.

In Vitro Transcription, Electroporation, Colony Formation Assays, and Quantitative RT-PCR.

The primers for detecting CyPA, CyPB, and CyPC have the following sequences: A-Forward, 5'-CGG GTC CTG GCA TCT TGT-3' (SEQ ID NO: 12) and A-Reverse, 5'-GCA GAT GAA AAA CTG GGA ACCA-3' (SEQ ID NO: 13); B-Forward, 5'-GGC CAA CGC AGG CAA A-3' (SEQ ID NO: 14) and B-Reverse, 5'-TCT AGC CAG GCT GTC TTG ACT GT-3' (SEQ ID NO: 15); C-Forward, 5'-GCT GAA GCA CTA TGG CAT TGG-3' (SEQ ID NO: 16) and C-Reverse, 5'-GAA CTG AGA GCC ATT GGT GTC A-3' (SEQ ID NO: 17).

Co-IP/RT-PCR.

Replicon cells ($5\times10^6$) are seeded into a T-75 flask (treated with 4 µg/ml CsA where indicated) 1 day before the immunoprecipitation (IP) experiment. Twenty-four hours later, cells are lysed in 1 ml of IP buffer (50 mM Tris-HCl, pH 8.0, 150 mM NaCl, 1 mM phenylmethylsulfonyl fluoride [PMSF], and 0.5% NP-40). Two hundred units of RNaseOUT (Invitrogen, Carlsbad, Calif.) are added to the supernatant after centrifugation at 12,000×g for 15 min. The supernatant is then added to 50 µl 75% protein G slurry containing either anti-CyPA or rabbit immunoglobulin G (IgG). The binding is allowed to proceed at 4° C. overnight, after which the protein G beads are washed with IP buffer four times. RNA is extracted from the beads with an RNeasy kit (Qiagen, Valencia, Calif.). RT-PCR is then used to detect HCV internal ribosome entry site (IRES) with the following primers: IRES Forward, 5'-GTC TGC GGA ACC GGT GAG-3'; (SEQ ID NO: 18); IRES Reverse, 5'-CGG GTT GAT CCA AGA AAG GAC-3' (SEQ ID NO: 19).

Recombinant Protein Production and GST Binding Assay.

Recombinant protein expression and purification via glutathione Sepharose 4B beads are carried out according to the manufacturer's protocol (GE Healthcare, Piscataway, N.J.). For the glutathione S-transferase (GST) pull-down assay, 20 µg of GST or GST-CyPA is brought to a final volume of 200 µl with binding buffer (20 mM Tris-HCl, pH 7.5, 100 mM KCl, 2 mM $CaCl_2$, 2 mM $MgCl_2$, 5 mM dithiothreitol [DTT], 0.5% NP-40, 0.5 mM PMSF, 5% glycerol). Replicon cells ($4\times10^5$) are lysed in 300 µl of IP buffer supplemented with 1 mM DTT and 1 mM EDTA, and 40 µl of this lysate is added to each sample and allowed to rotate at 4° C. for 30 min. Glutathione Sepharose 4B beads (25 µl of a 50% slurry per sample) are then added to each sample and allowed to rotate at 4° C. for 30 min. Beads are washed and then sedimented at 500×g for 5 min. Proteins bound to the beads are analyzed by sodium dodecyl sulfate-polyacrylamide gel electrophoresis (SDS-PAGE) and Western blotting. For the reactions that included CsA, the compound is added to the recombinant proteins prior to the addition of the cell lysates.

Co-IP of NS5B and CyPA.

293-T cells are transfected with cDNAs expressing Con1 NS5B and Flag-CyPA for 48 h. Cells are lysed in IP buffer (50 mM Tris-HCl, pH 8.0, 150 mM NaCl, 0.5% NP-40.1 mM PMSF, 1 mM EDTA, 1 mM DTT, 1× protease inhibitor cocktail) by rotating at 4° C. for 30 min. The lysate is then clarified by centrifugation, and the supernatant is subjected to IP with EZview anti-Flag M2 affinity beads (Sigma-Aldrich, Mo.) according to the manufacturer's instructions. Proteins bounds to the beads following the IP protocol are eluted by boiling in SDS loading buffer and analyzed by SDS-PAGE followed by Western blotting using the indicated antibodies.

JFH-1/HCVcc Production and Infection.

Full-length JFH-1 cDNA is provided by Takaji Wakita. Production of infectious HCVcc and infection of Huh-7.5 cells are performed as described previously (See, e.g., Zhong, J. et al., "Robust hepatitis C virus infection in vitro," *Proc. Natl. Acad. Sci. USA*, 102:9294-9299 (2005)). Western blotting and immunostaining of infected cells are carried out according to standard methods.

Electroporation of Replicon RNA and cDNA Expression Plasmids.

One microgram of replicon RNA is mixed with 9 µg of a pcDNA3.1-based plasmid containing no insert, CyPA cDNA, CyPB cDNA, or CyPC cDNA and used in a standard electroporation (36). RNA is extracted 7 h and 4 days post-electroporation and subjected to quantitative RT-PCR analysis to detect HCV RNA as described previously (See, e.g., Robida, J. M et al., Characterization of hepatitis C virus subgenomic replicon resistance to cyclosporine in vitro, *J. Virol.*, 81:5829-5840 (2007). All the CyP cDNAs are tagged with a Myc epitope at the C terminus, and the CyPA cDNA containing silent mutations in the sh-A159 recognition site is designated CyPA#.

In Vitro Replication Assay.

Replicon cells are washed with ice-cold wash buffer (30 mM HEPES [pH 7.4], 33 mM $NH_4Cl$, 7 mM KCl, 150 mM sucrose, 4.5 mM magnesium acetate) containing freshly added lysolecithin (250 µg/ml) for 2 min. After complete aspiration of the wash buffer, 125 µl of incomplete replication buffer (100 mM HEPES [pH 7.4], 50 mM $NH_4Cl$, 7 mM KCl, 1 mM spermidine) is added to each plate, and the cell lysates are collected with a cell scraper. The lysate is then centrifuged at 800×g for 5 min to remove cell debris, and the recovered supernatant is stored at −80° C. as replication lysates, 70 µl of which is used for each in vitro replication assay as described below. Before the replication assay is performed, NP-40 (1%, vol/vol) is added to each replication lysate and the mixture is rotated at 4° C. for 1 h, after which time 7 µl rabbit anti-CyPA polyclonal antibody or normal rabbit IgG (negative control) is added, and the mixture is rotated at 4° C. for an additional 4 h. In vitro replication is carried out for 4 h at 4° C. in the presence of actinomycin D (10 µg/ml); RNaseOUT (800 U/ml); 25 µCi α-$^{32}$P-labeled CTP; 10 µM CTP; and 1 mM each of ATP, GTP, and UTP. RNA is immediately extracted after replication with TRIzol LS (Invitrogen) as described by the manufacturer. The products of the reactions are electrophoresed on 1.2% agarose gels for 2 to 3 h, dried on a gel dryer, and exposed to a phosphorimaging screen for at least about 24 h.

Example 2

Figure 1B:
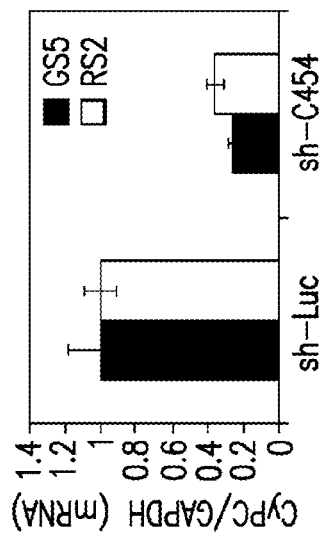
FIG. 1B is an image of Western blots showing expression of the proteins NS5A, CyPB, and CyPA in GS5 and RS2 replicon cells in response to various shRNAs (sh-Luc, sh-A159, sh-B710, or shi-C454) expressed for seven days prior to lysis.
Figure 1C:
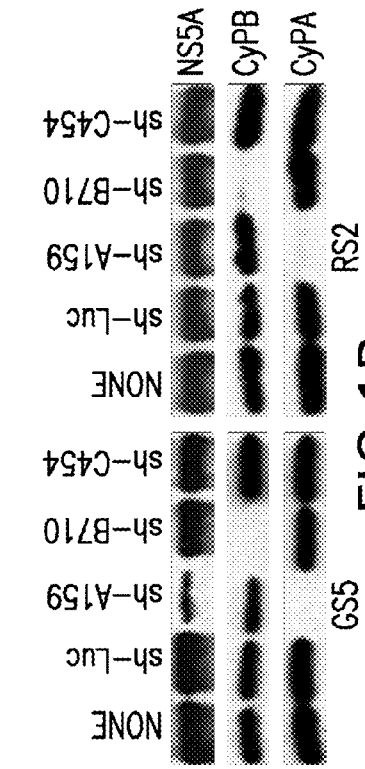
FIG. 1C is a bar graph illustrating suppression of CyPC RNA expression by sh-C454, relative to sh-Luc, as determined by real time RT-PCR, in GS5 and RS2 cells.
Figure 1D:
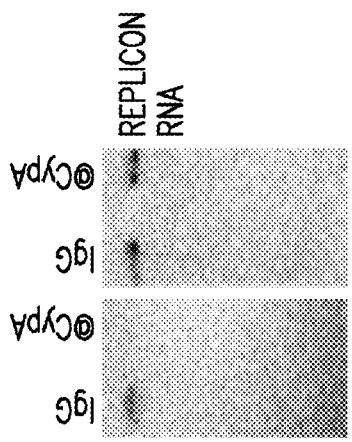
FIG. 1D is an image of plates containing GS5 and RS2 cells stained with violet blue after introduction of various shRNAs (sh-Luc, sh-A159, sh-B710, or sh-C454) into the cells and following double selection with puromycin and G418 and staining with violet blue.

A Small Interfering RNA (siRNA) Directed at Inhibiting CyPA Wild-Type but not CsA-Resistant HCV Replicons A HCV subgenomic replicons resistant to CsA treatment is isolated in vitro (see, Robida, J. M. et al., "Characterization of hepatitis C virus subgenomic replicon resistance to cyclosporine in vitro," *J. Virol.* 81:5829-5840 (2007)), the entire disclosure and contents of which is hereby incorporated by reference). Cells containing the RS2 replicon are resistant to CsA at up to 2 µg/ml, while the cells expressing the GS5 cells are inhibited by CsA at even 0.25 µg/ml (FIG. 1A). To investigate the mechanism of this resistance, the dependence of these replicons on the three CyPs (CyPA, -B, and -C) that have been implicated in HCV replication is examined The shRNAs expressed are directed at each of these CyPs along with a control shRNA directed at firefly luciferase in either the GS5 or RS2 cells. All three CyP-directed shRNAs efficiently knocked down the expressions of their respective targets (FIGS. 1B and C). The shRNA directed at CyPA (sh-A159) inhibits NS5A expression in GS5 cells but not in RS2 cells, despite similar knock-down levels of CyPA in the two cell lines. The shRNAs directed at CyPB (si-B710) or CyPC (sh-C454) has no effect on the NS5A level in either GS5 or RS2 cells. Fluorescence-activated cell sorting (FACS) results with green fluorescent protein (GFP) expression as a readout confirms these results. The same panel of shRNAs is also used in a colony formation assay designed to test their effects on HCV replication. The replicon cells are transduced with shRNA-expressing vectors that carry the puromycin N-acetyltransferase (pac) gene and then the cells are subjected to a double selection with both puromycin and G418, which selects for cells that maintain replication. When GS5 cells are transduced with sh-A159, a significantly lower number of double-resistant colonies are observed, reflecting the inhibitory effect of sh-A159 on GS5 replication. This lower colony formation efficiency is not observed in RS2 cells (FIG. 1D). On the other hand, shRNAs directed at CyPB and CyPC has no significant effect on the number of colonies. Similar results are obtained with a CsA-resistant replicon single-cell clone, RS1-2.

Figure 1E:
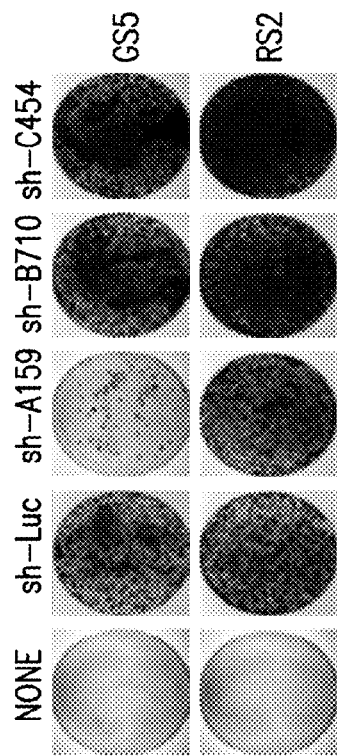
FIG. 1E is an image of an RNA gel showing $^{32}$P-labeled products of an in vitro replication reaction of GS5 or RS2 lysate allowed to progress in the presence of either a IgG negative control or an anti-CyPA antibody for 4 hours.

To further validate a role of CyPA protein in HCV replication, in vitro replication assays are performed with cell extracts of replicon cells and then tested the ability of an antibody against CyPA to interfere with replication. Anti-CyPA effectively blocks replication when the assay is performed with GS5 lysate but fails to inhibit replication if RS2 lysate is used (FIG. 1E). These data corroborate the RNA interference results and suggest that CyPA protein is important for a step in the HCV replication process that may be measured by the in vitro replication assay.

Example 3

HCV Replicon Expression is Correlated with CyPA Expression Level

Several other siRNAs directed at CyPA have been evaluated in vitro for anti-HCV effects. However, these studies have yielded conflicting results. Although two shRNAs directed at CyPA are reported to have both knocked down CyPA and inhibited replication of a GT 1b replicon. See, Nakagawa, M. et al., "Suppression of hepatitis C virus replication by cyclosporine a is mediated by blockade of cyclophilins," *Gastroenterology* 129:1031-1041 (2005). A CyPA siRNA that efficiently suppressed CyPA expression but fails to inhibit HCV replication is also reported. See, Watashi, K. et al., "Cyclophilin B is a functional regulator of hepatitis C virus RNA polymerase," *Mol. Cell.* 19:111-122 (2005).

In an attempt to reconcile these results and to develop a more robust siRNA composition against CyPA and HCV, shRNAs is constructed directed at the same CyPA mRNA sites as reported by these groups (FIG. 2A) and compares their effects on HCV replication to an embodiment of sh-A159 herein. The sh-285's target is the same 21-nucleotide sequence as Watashi's siRNA ("si-CyPA") and sh-459's is a 21-nucleotide sequence that is encompassed by Nakagawa's shRNA #441, which has a target sequence of 29 nucleotides. An sh-A285' is also constructed, which is identical to sh-285 except for a mismatch of one nucleotide between the siRNA and the target sequence. Consequently, sh-285' is expected to lack the ability to knock down CyPA. Finally, a negative-control shRNA (sh-NTC) is constructed that does not recognize any human mRNA in GenBank. When this panel of shRNAs is introduced into GS5 cells, three of them, sh-A159, sh-A285, and sh-A459, knock down CyPA expression as is expected (FIG. 2B). All three cell lines with CyPA knock-downs also have reduced NS5A levels. The shRNAs that do not inhibit CyPA expression also do not affect the replicon. Importantly, however, the original shRNA (sh-A159) embodiment is the most effective in both silencing CyPA expression and inhibiting NS5A synthesis (FIG. 2B).

Because the different effects of sh-A285 and Watashi's si-CyPA could potentially be explained by differences between shRNA and synthesized siRNA duplex, a synthesized form of sh-A159 and sh-A285 is tested in transient transfection experiments. Both siRNAs (si-A159 and si-A285) inhibited CyPA and NS5A expression (FIG. 2C). In this form, si-A159 is no more potent than si-A285 in suppressing CyPA expression; accordingly, the abilities of these two siRNAs to inhibit HCV replicon are also comparable. The overall reduction of both CyPA and NS5A levels is less dramatic with these preformed siRNA duplexes, likely due to the lower efficiency of transfecting siRNA into cells in comparison to transducing the shRNAs using lentiviral vectors. To eliminate definitively the possibility that the target of all these siRNAs is a chimeric mRNA containing the entire CyPA mRNA as part of its sequence (See, e.g., Sayah, D. M. et al., "Cyclophilin A retrotransposition into TRIMS explains owl monkey resistance to HIV-1," *Nature* 430:569-573 (2004)), cDNA rescue experiments are performed. A cDNA of CyPA that contains silent mutations in the recognition site of sh-A159 is constructed and cloned into a mammalian expression vector. A Myc tag is placed at the C-terminus of the protein to allow specific detection. When this cDNA (Myc-A#) is introduced into replicon cells together with sh-A159, both NS5A expression (FIG. 2D) and HCV RNA replication (FIG. 2E) are partially rescued, indicating that sh-A159 indeed exerts its inhibitory effect by repressing CyPA expression.

Example 4

CyPA Mediates CsA Resistance of RS2 Cells

Figure 3A:
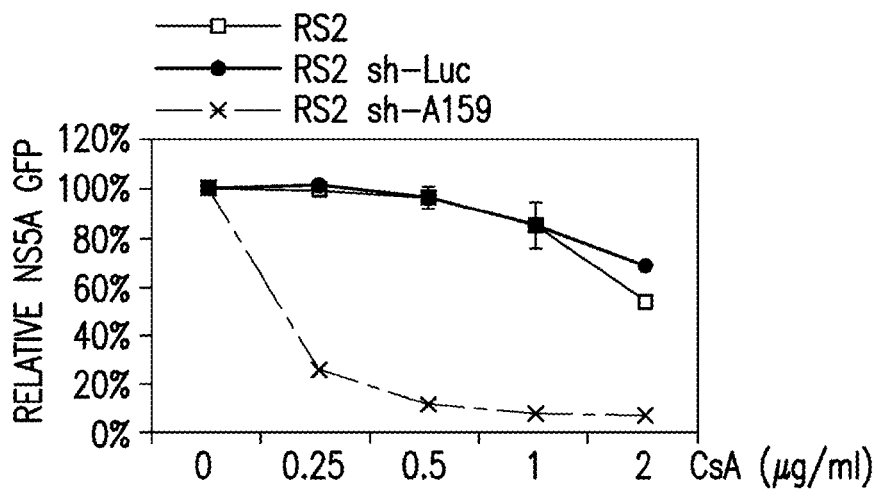
FIG. 3A is a graphical plot of the relative percentage of NS5A-GFP expression normalized to untreated sample from RS2 cells and two derivative cell lines stably expressing sh-Luc or sh-A159 and treated with increasing amounts of CsA for 4 days before being fixed for FACS analysis.
Figure 3B:
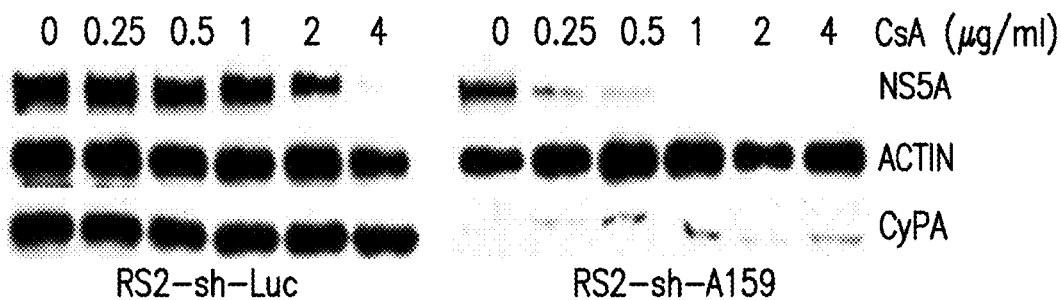
FIG. 3B is an image of Western blots showing expression of the proteins NS5A, Actin, and CyPA in RS2 cells expressing sh-Luc or sh-A159 following treatment with varying concentrations of CsA.
Figure 3C:
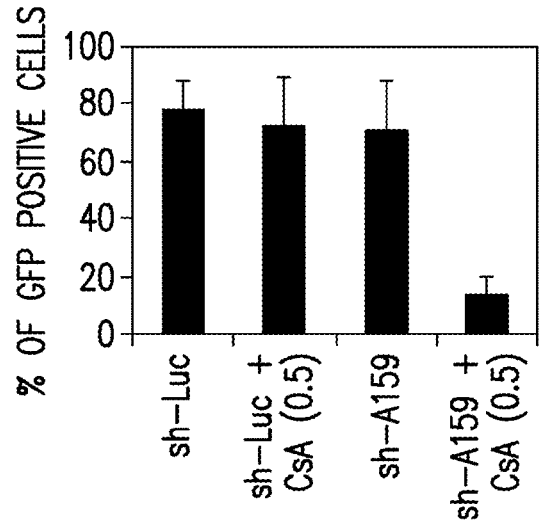
FIG. 3C is a bar graph showing the relative percentage of NS5A-GFP expressing RS2 cells transduced with either sh-Luc or sh-A159 for four days, with or without treatment with 0.5 µg/ml CsA for an additional 3 days, as determined by FACS analysis.

In contrast to the GS5 replicon, RS2 replicates efficiently in the presence of substantial CyPA knock-down (FIG. 1D). This result could be explained by either CyPA-independent replication or a replication strategy that requires much less CyPA protein because shRNAs normally cannot eliminate the gene product completely. To distinguish between these two possibilities, the RS2/sh-A159 replicon cells are treated, and recovered after double selection of puromycin and G418 following shRNA transduction, with CsA. If RS2 replicates in a CyP-independent manner in these cells, one would expect no effect of the CsA on the RS2/sh-A159 cells. On the other hand, if the RS2 replicon is resistant to CsA and sh-A159 because it needs less CyPA to replicate (thus requiring a higher concentration of CsA to inhibit its replication), then one would expect a reduced resistance to CsA as the pool of CyPA is smaller in this case. Indeed, the latter appears to be the case, as the RS2/sh-A159 replicon is six to eight times more sensitive to CsA than is the RS2/sh-Luc replicon (FIG. 3A), essentially reverting to the sensitivity level of the wild-type replicon GS5. Western blotting confirmed the substantial suppression of CyPA in the RS/sh-A159 cells (FIG. 3B). To control for the possibility that the difference in sensitivity to CsA is caused by some unidentified differences in the antibiotic-selected cells, a double treatment (sh-A159 and CsA) is applied to RS2 cells without selection. When the RS2 cells are treated with 0.5 µg/ml CsA or are transduced with sh-A159, no significant suppression is seen in either treatment, but when RS2 cells are first transduced with sh-A159 and are then treated with the same concentration of CsA, a dramatic inhibition is achieved (FIG. 3C). Taken together, these data indicate that CyPA is the principal mediator of the CsA resistance observed in RS2 cells, the replication of which requires a much reduced level of CyPA.

Example 5

CyPA is Essential for the Replication of Multiple HCV Isolates

GS5 and RS2 cells contain GT 1b replicons with the GFP gene inserted into the NS5A region. (See, e.g., Moradpour, D. et al., "Insertion of green fluorescent protein into nonstructural protein 5A allows direct visualization of functional hepatitis C virus replication complexes," J. Virol. 78:7400-7409 (2004); Nelson, H. B. et al., "Effect of cell growth on hepatitis C virus (HCV) replication and a mechanism of cell confluence-based inhibition of HCV RNA and protein expression," J. Virol. 80:1181-1190 (2006)). Next the effect of CyPA knock-down on replicons without GFP is examined. Both GT 1a and 1b replicons are tested. To this end, stable Huh-7.5 cell lines are established that express the various shRNAs and then challenges them, by electroporation, with in vitro-transcribed GT 1a (H77) and 1b (Con1) subgenomic replicon RNAs. The shRNAs effectively silence the expression of their respective targets in the stable cells as expected (FIGS. 4A and 4B). No defect in morphology or growth rate is detected for any of the stable cell lines, confirming that these CyPs are dispensable for cell survival in vitro. See, e.g., Braaten, D. et al., "Cyclophilin A regulates HIV-1 infectivity, as demonstrated by gene targeting in human T cells," EMBO J. 20:1300-1309 (2001). Expression of sh-A159 completely inhibits the ability of either replicon RNA to form colonies, whereas sh-Luc has no effect (FIG. 4C). An inhibitory effect (–50%) of sh-B710 on the GT 1a replicon is sometimes observed, but the colony formation efficiency is still much higher than that in sh-A159 cells. No other shRNA shows any consistent inhibitory effect on any of the replicons. Transient-transduction experiments again confirm the inhibitory effect of sh-A159 on the expression of NS5A of both GT 1a and 1b replicons (FIG. 4D).

The complete cycle of HCV infection can now be studied in cell culture with infectious viruses produced in vitro (see, e.g., Cai, Z. et al., "Robust production of infectious hepatitis C virus (HCV) from stably HCV cDNA-transfected human hepatoma cells," J. Virol. 79:13963-13973 (2005); Lindenbach, B. D. et al., "Complete replication of hepatitis C virus in cell culture," Science 309:623-626 (2005); Wakita, T. et al., "Production of infectious hepatitis C virus in tissue culture from a cloned viral genome," Nat. Med. 11:791-796 (2005); Yi, M. et al., "Production of infectious genotype 1a hepatitis C virus (Hutchinson strain) in cultured human hepatoma cells," PNAS 103:2310-2315 (2006); Zhong, J. et al., "Robust hepatitis C virus infection in vitro," PNAS 102:9294-9299 (2005)), the entire disclosures and contents of which are hereby incorporated by reference), so whether CyPA is required for HCV infection in vitro is determined next. Stable Huh-7.5 cells harboring control or sh-A159 are infected with HCVcc particles which are produced with the JFH-1 genome. Infection of Huh-7.5 cells is efficient; viral RNA and antigens become readily detectable in the target cells within a few days after infection. Expression of sh-Luc or sh-B710 has no effect on HCV infection, whereas the sh-A159 cells are highly refractory to infection (FIG. 5A). The protection provided by sh-A159 is observed by several methods: RT-PCR, fluorescence staining for core protein, or Western blot detection of NS3 (FIGS. 5B and C). The sh-A159 cells remains fully susceptible to infection by vesicular stomatitis virus, a negative-strand RNA virus that is sensitive to nonspecific antiviral responses (FIG. 5D).

Last, to determine whether sh-A159 could repress an existing infection, Huh-7.5 cells are infected with JFH-1 virus for 10 days and are then introduced sh-A159 by transduction. The expression of NS3 is measured 7 days after transduction. As shown in FIG. 5E, delivery of sh-A159 into infected cells suppresses viral replication, parallel to the results which are obtained with transient transduction of replicon cells.

Example 6

The Association of CyPA with HCV Polymerase and RNA in Replicon Cells is Correlated with CsA Resistance In vitro replication results suggests that CyPA is directly involved in the replication process (FIG. 1E). To determine whether CyPA is associated with HCV genome in replicon cells, CyPA are precipitated from replicon lysates and are extracted the coprecipitated RNA, which is then subjected to RT-PCR analysis with primers complementary to the 5' non-translated region of HCV. HCV RNA is found to be precipitated by an anti-CyPA antibody but not by an IgG control antibody (FIG. 6A). This association is inhibited by CsA treatment when the experiment is performed with the GS5 replicon (FIG. 6B, left). For the RS2 replicon, association with CyPA is resistant to CsA treatment (FIG. 6B, right). The interaction between CyPA and the HCV polymerase NS5B is examined next. GST-CyPA specifically binds NS5B while GST protein alone is not able to bind (FIG. 6C). The interaction between GS5 NS5B and GST-CyPA is reduced by CsA treatment and becomes abolished at 2.4 µg/ml CsA (FIG. 6D, left). NS5B from the RS2 cells, however, retains binding to GST-CyPA even at this concentration of the drug (FIG. 6D, right). These results suggest that the association of CyPA with the HCV replication machinery is targeted by CsA and the CsA-resistant interaction between NS5B and CyPA contributes to the CsA-resistant replication of the RS2 replicon. To examine if NS5B could interact with CyPA in vivo in the absence of any other HCV proteins and viral RNA, co-IP experiments are performed with NS5B and Flag-tagged CyPA transiently expressed in 293-T cells. NS5B coprecipitates with CyPA in this setting (FIG. 6E), indicating that the CyPA-NS5B interaction in vivo is not mediated by any other viral protein or RNA. Only a fraction of the total NS5B is precipitated by the anti-Flag beads as expected because the expressed NS5B proteins are expected to interact with both Flag-tagged and untagged, endogenous CyPA.

Example 7

Different Expression Levels of CyP Isoforms in Replicon Cells

Figure 7:
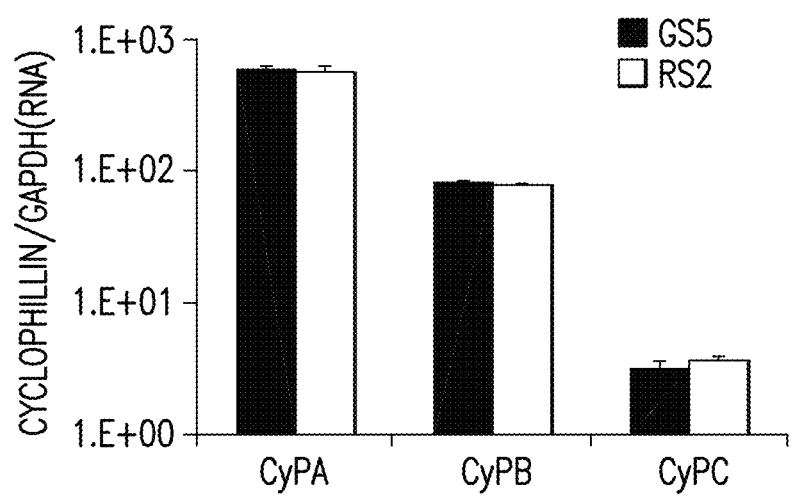
FIG. 7 is a bar graph showing the relative expression levels of CyPA, CyPB, and CyPC RNA in GS5 and RS2 replicon cells using real time PCR.

Consistent with the critical role of CyPA in mediating CsA's action in regulating a variety of biological activities such as immunosuppression (see, e.g., Handschumacher, R. E. et al., "Cyclophilin: a specific cytosolic binding protein for cyclosporine A," *Science* 226:544-547 (1984)), HIV infection (see, e.g., Braaten, D. et al., "Cyclophilin A regulates HIV-1 infectivity, as demonstrated by gene targeting in human T cells," *EMBO J.* 20:1300-1309 (2001)), and HCV replication, it has been shown that the expression level of CyPA is 10 to 100 times higher than that of other CyPs in various tissues (see, e.g., Bergsma, D. J. et al., "The cyclophilin multigene family of peptidyl-prolyl isomerases: Characterization of three separate human isoforms," *J. Biol. Chem.* 266:23204-23214 (1991)). The endogenous expression level of the three CyP isoforms in the replicon cells is examined Using quantitative RT-PCR and glyceraldehyde-3-phosphate dehydrogenase (GAPDH) mRNA as an internal control, a significant difference in the expression levels of CyPA, CyPB, and CyPC in the replicon cells is discovered. The CyPA mRNA is expressed approximately 10 and 150 times higher than CyPB and CyPC mRNAs, respectively (FIG. 7). Moreover, the expression levels of the CyPs are found to be very similar in GS5 and RS2 cells, ruling out the possibility that RS2 cells are more resistant to CsA because of higher endogenous level of CyPs.

For further discussion of various examples in the present applications, see, e.g., Yang, F. et al., "Cyclophilin A is an essential cofactor for hepatitis C virus infection and the principal mediator of cyclosporine resistance in vitro," *J. Virology* 82(11):5269-78 (2008), the entire disclosure and contents of which is hereby incorporated by reference.

All documents, patents, journal articles and other materials cited in the present application are hereby incorporated by reference in their entirety. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A DNA polynucleotide comprising a DNA sequence region encoding a sense RNA sequence that is at least about 70% homologous to at least 19 contiguous nucleotides between nucleotides 155 and 183 of human cyclophilin A sequence (SEQ ID NO: 1), wherein the sense RNA strand is from 19 to 29 nucleotides in length;

further comprising a DNA sequence region encoding an antisense RNA sequence that is complementary to the sense RNA sequence; and wherein the DNA polynucleotide is double-stranded and the DNA sequence region encoding a sense RNA sequence and the DNA sequence region encoding an antisense RNA sequence are base-paired with each other on opposing strands.

2. A plasmid vector, comprising the DNA polynucleotide of claim 1.

3. The plasmid vector of claim 2, further comprising a promoter, wherein the DNA sequence region encoding a sense RNA sequence is under the control of the promoter.

4. The plasmid vector of claim 3, wherein the promoter comprises an inducible promoter.

5. The plasmid vector of claim 3, wherein the promoter comprises a tissue-specific promoter.

6. The plasmid vector of claim 3, wherein the tissue-specific promoter comprises an albumin promoter.

7. The plasmid vector of claim 3, wherein the promoter comprises an RNA polymerase III promoter.

8. The plasmid vector of claim 7, wherein the RNA polymerase III promoter is selected from the group consisting of H1, U6, 5S, 7SK, and tRNA promoters.

9. A delivery composition, comprising the DNA polynucleotide of claim 1 in combination with a delivery reagent.

10. The delivery composition of claim 9, wherein the delivery reagent is selected from the group consisting of Minis Transit lipophilic reagent, lipofectin, lipofectamine, cellfectin, cationic polymers, cationic lipids, and liposomes.

11. The DNA polynucleotide of claim 1, further comprising a DNA sequence region encoding a hairpin sequence inserted between the DNA sequence region encoding a sense RNA sequence and the DNA sequence region encoding an antisense RNA sequence, such that the sense RNA sequence encoded by the DNA polynucleotide and the antisense RNA sequence encoded by the DNA polynucleotide are covalently attached by the hairpin sequence to form a shRNA.

12. The DNA polynucleotide of claim 11, wherein the shRNA encoded by the DNA polynucleotide comprises SEQ ID NO: 3.

13. A plasmid vector, comprising the DNA polynucleotide of claim 11.

14. The plasmid vector of claim 13, further comprising a promoter, wherein the DNA sequence regions encoding the shRNA are under the control of the promoter.

15. The plasmid vector of claim 14, wherein the promoter comprises an inducible promoter.

16. The plasmid vector of claim 14, wherein the promoter comprises a tissue-specific promoter.

17. The plasmid vector of claim 14, wherein the tissue-specific promoter comprises an albumin promoter.

18. The plasmid vector of claim 14, wherein the promoter comprises an RNA polymerase III promoter.

19. The plasmid vector of claim 18, wherein the RNA polymerase III promoter is selected from the group consisting of H1, U6, 5S, 7SK, and tRNA promoters.

20. A delivery composition, comprising the DNA polynucleotide of claim 11 in combination with a delivery reagent.

21. The delivery composition of claim 20, wherein the delivery reagent is selected from the group consisting of Minis Transit lipophilic reagent, lipofectin, lipofectamine, cellfectin, cationic polymers, cationic lipids, and liposomes.

* * * * *

SEQUENCE LISTING

```
<160> NUMBER OF SEQ ID NOS: 22

<210> SEQ ID NO 1
<211> LENGTH: 723
<212> TYPE: DNA
<213> ORGANISM: Homo sapiens

<400> SEQUENCE: 1
gtgtactatt agccatggtc aaccccaccg tgttcttcga cattgccgtc gacggcgagc      60
ccttgggccg cgtctccttt gagctgtttg cagacaaggt cccaaagaca gcagaaaatt     120
ttcgtgctct gagcactgga gagaaaggat ttggttataa gggttcctgc tttcacagaa     180
ttattccagg gtttatgtgt cagggtggtg acttcacacg ccataatggc actggtggca     240
agtccatcta tggggagaaa tttgaagatg agaacttcat cctaaagcat acgggtcctg     300
gcatcttgtc catggcaaat gctggaccca acacaaatgg ttcccagttt ttcatctgca     360
ctgccaagac tgagtggttg gatggcaagc atgtggtgtt tggcaaagtg aaagaaggca     420
tgaatattgt ggaggccatg gagcgctttg ggtccaggaa tggcaagacc agcaagaaga     480
tcaccattgc tgactgtgga caactcgaat aagtttgact tgtgttttat cttaaccacc     540
agatcattcc ttctgtagct caggagagca cccctccacc ccatttgctc gcagtatcct     600
agaatctttg tgctctcgct gcagttccct ttgggttcca tgttttcctt gttccctccc     660
atgcctagct ggattgcaga gttaagttta tgattatgaa ataaaaacta aataacaatt     720
gtc                                                                   723

<210> SEQ ID NO 2
<211> LENGTH: 21
<212> TYPE: RNA
<213> ORGANISM: Artificial Sequence
<220> FEATURE:
<223> OTHER INFORMATION: sense A-159

<400> SEQUENCE: 2
```

```
aaggguuccu gcuuucacag a                                              21

<210> SEQ ID NO 3
<211> LENGTH: 51
<212> TYPE: RNA
<213> ORGANISM: Artificial Sequence
<220> FEATURE:
<223> OTHER INFORMATION: sh-A159

<400> SEQUENCE: 3
aaggguuccu gcuuucacag auucaagaga ucugugaaag caggaacccu u             51

<210> SEQ ID NO 4
<211> LENGTH: 21
<212> TYPE: RNA
<213> ORGANISM: Artificial Sequence
<220> FEATURE:
<223> OTHER INFORMATION: antisense A-159

<400> SEQUENCE: 4
ucugugaaag caggaacccu u                                              21

<210> SEQ ID NO 5
<211> LENGTH: 51
<212> TYPE: DNA
<213> ORGANISM: Artificial Sequence
<220> FEATURE:
<223> OTHER INFORMATION: sh-A159 template

<400> SEQUENCE: 5
ttcccaagga cgaaagtgtc taagttctct agacactttc gtccttggga a             51

<210> SEQ ID NO 6
<211> LENGTH: 21
<212> TYPE: DNA
<213> ORGANISM: Artificial Sequence
<220> FEATURE:
<223> OTHER INFORMATION: sense A-159

<400> SEQUENCE: 6
aagggttcct gctttcacag a                                              21

<210> SEQ ID NO 7
<211> LENGTH: 21
<212> TYPE: DNA
<213> ORGANISM: Artificial Sequence
<220> FEATURE:
<223> OTHER INFORMATION: sense A-285

<400> SEQUENCE: 7
aagcatacgg gtcctggcat c                                              21

<210> SEQ ID NO 8
<211> LENGTH: 21
<212> TYPE: DNA
<213> ORGANISM: Artificial Sequence
<220> FEATURE:
<223> OTHER INFORMATION: sense A-285'

<400> SEQUENCE: 8
aagcatacag gtcctggcat c                                              21

<210> SEQ ID NO 9
<211> LENGTH: 21
<212> TYPE: DNA
<213> ORGANISM: Artificial Sequence
```

```
<220> FEATURE:
<223> OTHER INFORMATION: sense A-459

<400> SEQUENCE: 9
aatggcaaga ccagcaagaa g                                              21

<210> SEQ ID NO 10
<211> LENGTH: 21
<212> TYPE: DNA
<213> ORGANISM: Artificial Sequence
<220> FEATURE:
<223> OTHER INFORMATION: sense C-454

<400> SEQUENCE: 10
aagactgaag gtgtgctggt a                                              21

<210> SEQ ID NO 11
<211> LENGTH: 21
<212> TYPE: DNA
<213> ORGANISM: Artificial Sequence
<220> FEATURE:
<223> OTHER INFORMATION: No target control (NTC) sequence

<400> SEQUENCE: 11
aaggaggtga catcaccact g                                              21

<210> SEQ ID NO 12
<211> LENGTH: 18
<212> TYPE: DNA
<213> ORGANISM: Homo sapiens

<400> SEQUENCE: 12
cgggtcctgg catcttgt                                                  18

<210> SEQ ID NO 13
<211> LENGTH: 22
<212> TYPE: DNA
<213> ORGANISM: Homo sapiens

<400> SEQUENCE: 13
gcagatgaaa aactgggaac ca                                             22

<210> SEQ ID NO 14
<211> LENGTH: 16
<212> TYPE: DNA
<213> ORGANISM: Homo sapiens

<400> SEQUENCE: 14
ggccaacgca ggcaaa                                                    16

<210> SEQ ID NO 15
<211> LENGTH: 23
<212> TYPE: DNA
<213> ORGANISM: Homo sapiens

<400> SEQUENCE: 15
tctagccagg ctgtcttgac tgt                                            23

<210> SEQ ID NO 16
<211> LENGTH: 21
<212> TYPE: DNA
<213> ORGANISM: Homo sapiens

<400> SEQUENCE: 16
gctgaagcac tatggcattg g                                              21
```

```
<210> SEQ ID NO 17
<211> LENGTH: 21
<212> TYPE: DNA
<213> ORGANISM: Homo sapiens

<400> SEQUENCE: 17
gaactgagag ccattggtgt c                                              21

<210> SEQ ID NO 18
<211> LENGTH: 18
<212> TYPE: DNA
<213> ORGANISM: Homo sapiens

<400> SEQUENCE: 18
gtctgcggaa ccggtgag                                                  18

<210> SEQ ID NO 19
<211> LENGTH: 21
<212> TYPE: DNA
<213> ORGANISM: Homo sapiens

<400> SEQUENCE: 19
cgggttgatc caagaaagga c                                              21

<210> SEQ ID NO 20
<211> LENGTH: 21
<212> TYPE: RNA
<213> ORGANISM: Artificial Sequence
<220> FEATURE:
<223> OTHER INFORMATION: antisense A-285

<400> SEQUENCE: 20
gaugccagga cccguaugcu u                                              21

<210> SEQ ID NO 21
<211> LENGTH: 21
<212> TYPE: RNA
<213> ORGANISM: Artificial Sequence
<220> FEATURE:
<223> OTHER INFORMATION: antisense A-285'

<400> SEQUENCE: 21
gaugccagga ccuguaugcu u                                              21

<210> SEQ ID NO 22
<211> LENGTH: 21
<212> TYPE: RNA
<213> ORGANISM: Artificial Sequence
<220> FEATURE:
<223> OTHER INFORMATION: antisense A-459

<400> SEQUENCE: 22
cuucuugcug gucuugccau u                                              21
```